United States Patent
Caimi et al.

(10) Patent No.: US 7,524,660 B2
(45) Date of Patent: Apr. 28, 2009

(54) UTILIZATION OF FRUCTOSE IN MICROBIAL PRODUCTION STRAINS

(75) Inventors: Perry Caimi, Kennett Square, PA (US); Charles Nakamura, Claymont, DE (US)

(73) Assignee: E.I. du Pont de Nemours and Company, Wilmington, DE (US)

(*) Notice: Subject to any disclaimer, the term of this patent is extended or adjusted under 35 U.S.C. 154(b) by 0 days.

(21) Appl. No.: 11/122,811

(22) Filed: May 5, 2005

(65) Prior Publication Data
US 2006/0252136 A1  Nov. 9, 2006

(51) Int. Cl.
| | |
|---|---|
| C12P 7/20 | (2006.01) |
| C12P 21/00 | (2006.01) |
| C12N 15/00 | (2006.01) |
| C12N 9/10 | (2006.01) |
| C12N 1/21 | (2006.01) |
| C07K 14/00 | (2006.01) |
| C07H 21/00 | (2006.01) |

(52) U.S. Cl. .................. 435/159; 435/69.1; 435/320.1; 435/252.3; 435/252.33; 435/440; 435/193; 530/350; 536/23.2

(58) Field of Classification Search .................. 435/159, 435/69.1, 320.1, 252.3, 252.33, 440, 193; 530/350; 536/23.2
See application file for complete search history.

(56) References Cited

U.S. PATENT DOCUMENTS

| | | | |
|---|---|---|---|
| 4,683,202 | A | 7/1987 | Mullis |
| 5,686,276 | A | 11/1997 | Laffend et al. |
| 6,013,494 | A | 1/2000 | Nakamura et al. |
| 6,136,576 | A | 10/2000 | Diaz-Torres et al. |
| 6,316,232 | B1 | 11/2001 | Sprenger et al. |
| 2001/0049126 | A1 | 12/2001 | Livshits et al. |
| 2004/0152174 | A1 | 8/2004 | Cervin et al. |

FOREIGN PATENT DOCUMENTS

| | | |
|---|---|---|
| EP | 1 149 911 A2 | 10/2001 |
| WO | WO 96/35796 A1 | 11/1996 |
| WO | WO 98/18937 A1 | 5/1998 |
| WO | WO 98/21339 | 5/1998 |
| WO | WO 98/21341 A2 | 5/1998 |
| WO | WO 99/28480 A1 | 6/1999 |
| WO | WO 01/12833 | 2/2001 |
| WO | WO 2004/033471 A2 | 4/2004 |
| WO | WO 2004/056963 A2 | 7/2004 |

OTHER PUBLICATIONS

U.S. Appl. No. 10/420,587, filed Apr. 22, 2003, Mark S. Payne et al.
J. Stulke et. al., Carbon Catabolite Repression in Bacteria, Curr. Opin. Microbiol., 1999, pp. 195-201, vol. 2.
Mechanism and Regulation of Carbohydrate Transport in Bacteria, 1985, Academic Press, New York, M.H. Saier ED., pp. 70-74.
F. Jacob et. al., Genetic Regulatory Mechanisms in the Synthesis of Proteins, J. Mol. Biol., 1961, pp. 318-358, vol. 3.
J.F. McGuinnis et. al., Catabolite Inhibition: A General Phenomenon in the Control of Carbohydrate Utilization, J. Bacteriol., 1969, pp. 902-913, vol. 100.
Juana M. Gancedo, Yeast Carbon Catabolite Repression, Microbiol. Mol. Biol. Rev., 1998, pp. 334-361, vol. 62.
N. Flores et. al., Pathway Engineering for the Production of Aromatic Compounds in *Escherichia coli*, Nat. Biotechnol., 1996, pp. 620-623, vol. 14.
R. Chen et. al., Metabolic Consequences of Phosphotransferase (PTS) Mutation in a Phenylalanine-Producing Recombinant *Escherichia coli*, Biotechnol. Prog., 1997, pp. 768-775, vol. 13.
Weisser et. al., Functional Expression of the Glucose Transporter of *Zymomonas mobilis* Leads to Restoration Of Glucose and Fructose Uptake in *Escherichia coli* Mutants and Provides Evidence for its Facilitator Action, J. Bacteriol., 1995, pp. 3351-3354, vol. 177.
Daniel et. al., Biochemistry of Coenzyme B12-Dependent Glycerol and Diol Dehydratases and Organization of the Encoding Genes, FEMS Microbiol. Rev., 1999, pp. 553-566, vol. 22.
Toraya et. al., A Reactivating Factor for Coenzyme B12 Dependent-Diol Dehydratase, J. Biol. Chem., 1999, pp. 3372-3377, vol. 274.
Tobimatsu et. al., Identification and Expression of the Genes Encoding A Reactivating Factor for Adenosylcobalamin-Dependent Glycerol Dehydratase, J. Bateriol., 1999, pp. 4110-4113, vol. 181.
E.A. Johnson et. al., Klebsiella Pneumoniae 1,3-Propanediol: NAD Oxidoreductase, J. Bacteriol., 1987, pp. 2050-2054, vol. 169.

(Continued)

*Primary Examiner*—Delia M Ramirez
(74) *Attorney, Agent, or Firm*—Christine M. Lhulier

(57) ABSTRACT

A process has been developed for the utilization of fructose by PTS⁻ microorganisms. Providing the microorganisms with increased fructokinase activity, and optionally with increased fructose transport capacity, allows the microorganisms to use fructose as a nutrient supply with sustained growth. The microbial production of substances such as cell mass, glycerol, and 1,3-propanediol may be achieved during growth in a fructose containing medium using this process.

17 Claims, No Drawings

OTHER PUBLICATIONS

Daniel et. al., Purification of 1,3-Propanediol Dehydrogenase from Citrobacter Freundii and Cloning, Sequencing, and Overexpression of Corresponding Gene in *Escherichia coli*, J. Bacteriol., 1995, pp. 2151-2156, vol. 177.

Luers et. al., Glycerol Conversion to 1,3-Propanediol by Clostridium Pasteurianum: Cloning and Expression of the Gene Encoding 1,3-Propanediol Dehydrogenase, FEMS Microbiol Lett., 1997, pp. 337-345, vol. 154.

Veiga Da Dunha et. al., 1,3-Propanediol: NAD Oxidoreductases of *Lactobacillus brevis* and *Lactobacillus buchneri*, Appl. Environ. Microbiol., 1992, pp. 2005-2010, vol. 58.

J. Sambrook et. al., Molecular Cloning: A Laboratory Manual, Second Edition, Cold Spring Harbor Laboratory Press, Cold Spring Harbor, 1989 (Book Not Suppled).

Altschul et. al., Basic Local Alignment Search Tool. J. Mol. Biol., 1993, pp. 403-410, vol. 215.

A.M. Lesk, Computational Molecular Biology, ED; Oxford University Press, New York, 1988 (Book Not Supplied).

D.W. Smith, Biocomputing: Informatics and Genome Projects, ED.; Academic Press, New York, 1993 (Book Not Supplied).

A.M. Griffin et. al., Computer Analysis of Sequence Data, Part 1, EDS.; Human Press, New Jersey, 1994 (Book Not Supplied).

G. Von Heinge, Sequence Analysis in Molecular Biology, EDS.; Academic Press, New York, 1987 (Book Not Supplied).

M. Gribskov et. al., Sequence Analysis Primer, EDS.; Stockton Press, New York, 1991 (Book Not Supplied).

Devereux et. al., A Comprehensive Set of Sequence Analysis Programs for the VAX, Nucleic Acids.Res., 1984, pp. 387-395, vol. 12.

Pearson et. al., Improved Tools for Biological Sequence Comparison, Proc. Natl. Acad. Sci. USA, 1988, pp. 2444-2448, vol. 85.

Stephen F. Altschul et. al., Gapped Blast and PSI-Blast: A New Generation of Protein Database Search Programs, Nucleic Acids Res., 1997, pp. 3389-3402, vol. 25.

Hein et. al., Unified Approach to Alignment and Phylogenies, Methods Enzymol., 1990, pp. 628-645, vol. 183.

H. Kornberg, It at First You Don't Succeed Fructose Utilization by *Escherichia coli*, Adv. Enz. Reg., 2002, pp. 349-360, vol. 42.

Francois Baneyx, Recombinant Protein Expression in *Escherichia coli*, Curr. Opin. Biotechnol., 1999, pp. 411-421, vol. 10.

Ross et. al., *Escherichia coli* Promoters With Up Elements of Different Strengths: Modular Structure of Bacterial Promotors, J. Bacteriol., 1998, pp. 5375-5383, vol. 180.

De Haseth et. al., RNA Polymerase-Promotor Interactions: The Comings and Goings of RNA Polymerase, J. Bacteriol., 1998, pp. 3019-3025, vol. 180.

Smolke et. al., Effect of Gene Location, MRNA Secondary Structures, and RNASE Sites on Expression of Two Genes in an Engineered Operon, Biotechnol. Bioeng., 2002, pp. 762-776, vol. 80.

Swartz, Advances in *Escherichia coli* Production of Therapeutic Proteins, Curr, Opin, Biotech., 2001, pp. 195.201, vol. 12.

Ma et. al., Correlations Between Shine-Dalgarno Sequences and Gene Features Such as Predicted Expression Levels and Operon Structures, J. Bacteriol., 2002, pp. 5733-5745, vol. 184.

Deshpande et. al., Appl. Ethanol Production From Cellulose by Coupled Saccharification/Fermentation Using *Saccharomuces cerevisiae* and Cellulase Complex From *Sclertium rolfsii* UV-8 Mutant, Biochem. Biotechnol., 1992, pp. 227-234, vol. 36.

Brock et. al., Increasing Alcohol Yield by Selected Yeast Fermentation of Sweet Sorghum. II. Isolation and Evaluation of Mutants and Wild Types for Ethanol Production, Food. Chem., 1984, pp. 313-318, vol. 14.

Phillipp Gerhardt et. al., Manual of Methods for General Bacteriology, American Society for Microbiology, 1994 (Book Not Supplied).

E.K. Jagusztyn-Krynicka et. al., Expression of Streptococcus Mutants Aspartate-Semialdehyde Dehydrogenase Gene Cloned Into Plasmid PBR322, J. Gen. Microbiol., 1982, pp. 1135-1145, vol. 128.

Sato et. al., Isolation, Characterization and Sequence Analysis of the SCRK Gene Encoding Fructokinase of Streptococcus Mutans, J. Gen. Microbiol., 1993, pp. 921-927, vol. 139.

M. Bradford, A Rapid and Sensitive Method for the Quantitation Of Microgram Quantities of Protein Utilizing the Principle of Protein-Dye Binding, Anal. Biochem., 1976, pp. 248-254, vol. 72.

J.H. Leua, A Short Course in Bacterial Genetics, Cold Spring Harbor, NY: Cold Spring Harbor Laboratory, 1992 (Book Not Supplied).

Wood et. al., The Genome of the Natural Genetic Engineer Agrobacterium Tumefaciens C58, Science, vol. 294, 2001, pp. 2317-2323.

Datsenko et. al., One-Step Inactivation of Chromosomal Genes in *Escherichia coli* K-12 Using PCR Products, Proc. Natl. Acad. Sci. USA, 2000, pp. 6640-6645, vol. 97.

National Center for Biotechnology General Identifier No. 48994873, Jun. 24, 2004, Accession No. U00096, F.R. Blattner et. al., the Complete Genome Sequence of *Escherichia coli* K-12.

National Center for Biotechnology Information General Identifier No. 145447, Apr. 26, 1993, Accession No. M21528, M.D. Lundrigan et. al., Altered Cobalamin Metabolism in *Escherichia coli* BTUR Mutants Affects BTUB Gene Regulation.

National Center for Biotechnology Information General Identifier No. 153885, Sep. 1, 1993, Accession No. L08890, S.J. Suh et. al., Cloning, Sequencing and Overexpression of Coba Which Encodes ATP: Corrinoid Adenosyltransferase in *Salmonella typhimurium*.

National Center for Biotechnology Information General Identifier No. 151150, Apr. 26, 1993, Accession No. M62866, J. Crouzet et. al., Nucleotide Sequence and Genetic Analysis of A 13.1-Kilobase-Pair Pseudomonas Denitrificans DNA Fragment Containing Five COB Genes and Identification of Structural Genes Encoding COB(I) Alamin Adenosyltransferase, Cobyric Acid Synthase, and Bifunctional Cobinamide Kinase-Cobinamide Phosphate Guanylyltransferase.

National Center for Biotechnology Information General Identifier No. 1430993, Apr. 18, 2005, Accession No. Z74071.

National Center for Biotechnology Information General Identifier No. 511134, Mar. 5, 1996, Accession No. Z35169, P. Eriksson et. al., Cloning and Characterization of GPD2, A Second Gene Encoding SN-Glycerol 3-Phosphate Denydrogenase (NAD+) In *Saccharomyces cerevisiae*, and Its Comparison With GPD1.

National Center for Biotechnology Information General Indentifier No. 984182, Apr. 18, 2005, Accession No. CAA62526, G. Mannhaupt et. al., Analysis of A 26 KB Region on the Left Arm of Yeast Chromosome XV.

National Center for Biotechnology Information General Identifier No. 466746, Mar. 25, 1994, Accession No. AAB18585, H.J. Sofia et. al., Analysis of the *Escherichia coli* Genome. V. DNA Sequence of the Region From 76.0 To 81.5 Minutes.

National Center for Biotechnology Information General Identifier No. 557761, Apr. 18, 2005, Accession No. Z38059 and Z47047, B. Barrell et. al., *Saccharomycetaceae cerevisiae* Chromosome IX Sequencing Project, MRC Laboratory of Molecular Biology, Hills RD, Cambridge.

National Center for Biotechnology Information General Identifier No. 147838, Apr. 26, 1993, Accession No. AAA24636, D. Austin et. al., Nucleotide Sequence of the GLPD Gene Encoding Aerobic SN-Glycerol 3-Phosphate Dehydrogenase of *Escherichia coli* K-12.

National Center for Biotechnology Information General Identifier No. 146176, Dec. 20, 1995, Accession No. M20938, S.T. Cole et. al., Nucleotide Sequence and Gene-Polypeptide Relationships of the GLPABC Operon Encoding the Anaerobic SN-Glycerol-3-Phosphate Dehydrogenase of *Escherichia coli* K-12.

National Center for Biotechnology Information General Identifier No. 1381127, Oct. 10, 2000, Accession No. U18813, F.S. Dietrich et. al., The Nucleotide Sequence of *Saccharomyces cerevisiae* Chromosome V.

National Center for Biotechnology Information General Identifier No. 2289854, Aug. 1, 1997, Accession No. U11583, T. Favello, The Sequence Of *S. cerevisiae* COSMID 9196.

National Center for Biotechnology Information General Identifier No. 304961, Aug. 12, 2002, Accession No. L19201, G. Plunkett et. al., Analysis of the *Escherichia coli* Genome. III. DNA Sequence of the Region From 87.2 to 89.2 Minutes.

National Center for Biotechnology Information General Identifier No. 409785, Dec. 17, 1993, Accession No. U00006, F.R. Blattner et.

al., Analysis of the *Escherichia coli* Genome. IV. DNA Sequence of the Region From 89.2 to 92.8 Minutes.

Hans Kornberg, if at First You Don't Succeed . . . Fructose Utilization by *Escherichia coli*, Advan. Enzyme Regul., vol. 42:349-360,, 2002.

Cristina I. Caescu et al., Bifidobacterium Longum Requires A Fructokinase (FRK; ATP:D-Fructose 6-Phosphotransferase, EC 2.7.1.4) for Fructose Catabolism, Journal of Bacteriology, vol. 186(19):6515-6525, 2004.

SEQUENCE LISTING

<160> NUMBER OF SEQ ID NOS: 14

```
<210> SEQ ID NO 1
<211> LENGTH: 13402
<212> TYPE: DNA
<213> ORGANISM: artificial sequence
<220> FEATURE:
<223> OTHER INFORMATION: plasmid

<400> SEQUENCE: 1
tagtaaagcc ctcgctagat tttaatgcgg atgttgcgat tacttcgcca actattgcga      60
taacaagaaa aagccagcct tcatgatat atctcccaat ttgtgtaggg cttattatgc     120
acgcttaaaa ataataaaag cagacttgac ctgatagttt ggctgtgagc aattatgtgc    180
ttagtgcatc taacgcttga gttaagccgc gccgcgaagc ggcgtcggct tgaacgaatt    240
gttagacatt atttgccgac taccttggtg atctcgcctt tcacgtagtg gacaaattct    300
tccaactgat ctgcgcgcga ggccaagcga tcttcttctt gtccaagata agcctgtcta    360
gcttcaagta tgacgggctg atactgggcc ggcaggcgct ccattgccca gtcggcagcg    420
acatccttcg gcgcgatttt gccggttact gcgctgtacc aaatgcggga caacgtaagc    480
actacatttc gctcatcgcc agcccagtcg ggcggcgagt tccatagcgt taaggtttca    540
tttagcgcct caaatagatc ctgttcagga accggatcaa agagttcctc cgccgctgga    600
cctaccaagg caacgctatg ttctcttgct tttgtcagca agatagccag atcaatgtcg    660
atcgtggctg gctcgaagat acctgcaaga atgtcattgc gctgccattc tccaaattgc    720
agttcgcgct tagctggata acgccacgga atgatgtcgt cgtgcacaac aatggtgact    780
tctacagcgc ggagaatctc gctctctcca ggggaagccg aagtttccaa aaggtcgttg    840
atcaaagctc gccgcgttgt ttcatcaagc cttacggtca ccgtaaccag caaatcaata    900
tcactgtgtg gcttcaggcc gccatccact gcggagccgt acaaatgtac ggccagcaac    960
gtcggttcga gatggcgctc gatgacgcca actacctctg atagttgagt cgatacttcg   1020
gcgatcaccg cttccctcat gatgtttaac tttgttttag ggcgactgcc ctgctgcgta   1080
acatcgttgc tgctccataa catcaaacat cgacccacgg cgtaacgcgc ttgctgcttg   1140
gatgcccgag gcatagactg taccccaaaa aaacagtcat aacaagccat gaaaaccgcc   1200
actgcgccgt taccaccgct gcgttcggtc aaggttctgg accagttgcg tgagcgcata   1260
cgctacttgc attacagctt acgaaccgaa caggcttatg tccactgggt tcgtgccttc   1320
atccgtttcc acggtgtgcg tcacccggca accttgggca gcagcgaagt cgaggcattt   1380
ctgtcctggc tggcgaacga gcgcaaggtt tcggtctcca cgcatcgtca ggcattggcg   1440
gccttgctgt tcttctacgg caaggtgctg tgcacggatc tgccctggct tcaggagatc   1500
ggaagacctc ggccgtcgcg gcgcttgccg gtggtgctga cccggatga agtggttcgc    1560 atcctcggtt ttctggaagg cgagcatcgt ttgttcgccc agcttctgta tggaacgggc   1620
atgcggatca gtgagggttt gcaactgcgg gtcaaggatc tggatttcga tcacggcacg   1680
atcatcgtgc gggagggcaa gggctccaag gatcgggcct tgatgttacc cgagagcttg   1740
gcacccagcc tgcgcgagca ggggaattaa ttcccacggg ttttgctgcc cgcaaacggg   1800
ctgttctggt gttgctagtt tgttatcaga atcgcagatc cggcttcagc cggtttgccg   1860
gctgaaagcg ctatttcttc cagaattgcc atgattttt ccccacggga ggcgtcactg   1920
gctcccgtgt tgtcggcagc tttgattcga taagcagcat cgcctgtttc aggctgtcta   1980
tgtgtgactg ttgagctgta acaagttgtc tcaggtgttc aatttcatgt tctagttgct   2040
ttgttttact ggtttcacct gttctattag gtgttacatg ctgttcatct gttacattgt   2100
```

```
cgatctgttc atggtgaaca gctttgaatg caccaaaaac tcgtaaaagc tctgatgtat   2160 ctatctttt tacaccgttt tcatctgtgc atatggacag ttttcccttt gatatgtaac    2220
ggtgaacagt tgttctactt ttgtttgtta gtcttgatgc ttcactgata gatacaagag   2280
ccataagaac ctcagatcct tccgtattta gccagtatgt tctctagtgt ggttcgttgt   2340
ttttgcgtga gccatgagaa cgaaccattg agatcatact tactttgcat gtcactcaaa   2400
aattttgcct caaaactggt gagctgaatt tttgcagtta aagcatcgtg tagtgttttt   2460
cttagtccgt tatgtaggta ggaatctgat gtaatggttg ttggtatttt gtcaccattc   2520 attttatct ggttgttctc aagttcggtt acgagatcca tttgtctatc tagttcaact    2580
tggaaaatca acgtatcagt cgggcggcct cgcttatcaa ccaccaattt catattgctg   2640
taagtgttta atctttact tattggttc aaaacccatt ggttaagcct tttaaactca     2700
tggtagttat tttcaagcat taacatgaac ttaaattcat caaggctaat ctctatattt   2760
gccttgtgag ttttctttg tgttagttct tttaataacc actcataaat cctcatagag    2820
tatttgtttt caaaagactt aacatgttcc agattatatt ttatgaattt ttttaactgg   2880
aaaagataag gcaatatctc ttcactaaaa actaattcta attttcgct tgagaacttg     2940 gcatagtttg tccactggaa aatctcaaag cctttaacca aaggattcct gatttccaca   3000
gttctcgtca tcagctctct ggttgcttta gctaatacac cataagcatt tccctactg    3060 atgttcatca tctgagcgta ttggttataa gtgaacgata ccgtccgttc tttccttgta   3120
gggttttcaa tcgtggggtt gagtagtgcc acacagcata aaattagctt ggtttcatgc   3180
tccgttaagt catagcgact aatcgctagt tcatttgctt tgaaaacaac taattcagac   3240
atacatctca attggtctag gtgattttaa tcactatacc aattgagatg ggctagtcaa   3300
tgataattac tagtcctttt cctttgagtt gtgggtatct gtaaattctg ctagacctt    3360 gctggaaaac ttgtaaattc tgctagaccc tctgtaaatt ccgctagacc tttgtgtgtt   3420 tttttgttt atattcaagt ggttataatt tatagaataa agaaagaata aaaaagata     3480 aaagaatag atcccagccc tgtgtataac tcactacttt agtcagttcc gcagtattac    3540
aaaaggatgt cgcaaacgct gtttgctcct ctacaaaaca gaccttaaaa ccctaaaggc   3600
ttaagtagca ccctcgcaag ctcgggcaaa tcgctgaata ttccttttgt ctccgaccat   3660
caggcacctg agtcgctgtc ttttttcgtga cattcagttc gctgcgctca cggctctggc  3720
agtgaatggg ggtaaatggc actacaggcg ccttttatgg attcatgcaa ggaaactacc   3780
cataatacaa gaaaagcccg tcacgggctt ctcagggcgt tttatggcgg gtctgctatg   3840
tggtgctatc tgacttttg ctgttcagca gttcctgccc tctgattttc cagtctgacc    3900
acttcggatt atcccgtgac aggtcattca gactggctaa tgcacccagt aaggcagcgg   3960
tatcatcaac aggcttaccc gtcttactgt cgggaattca tttaaatagt caaaagcctc   4020
cgaccggagg cttttgactg ctaggcgatc tgtgctgttt ccacggtat gcagcaccag    4080 cgcgagatta tgggctcgca cgctcgactg tcggacgggg gcactggaac gagaagtcag   4140
gcgagccgtc acgcccttga caatgccaca tcctgagcaa ataattcaac cactaaacaa   4200
atcaaccgcg tttccggag gtaaccaagc ttgcgggaga gaatgatgaa caagagccaa    4260
caagttcaga caatcaccct ggccgccgcc agcaaatgg cggcggcggt ggaaaaaaaa    4320
gccactgaga tcaacgtggc ggtggtgttt tccgtagttg accgcggagg caacacgctg   4380
cttatccagc ggatggacga ggccttcgtc tccagctgcg atatttccct gaataaagcc   4440
tggagcgcct gcagcctgaa gcaaggtacc catgaaatta cgtcagcggt ccagccagga   4500
```

```
caatctctgt acggtctgca gctaaccaac caacagcgaa ttattatttt tggcggcggc    4560
ctgccagtta ttttaatga gcaggtaatt ggcgccgtcg gcgttagcgg cggtacggtc    4620
gagcaggatc aattattagc ccagtgcgcc ctggattgtt tttccgcatt ataacctgaa    4680
gcgagaaggt atattatgag ctatcgtatg ttccgccagg cattctgagt gttaacgagg    4740
ggaccgtcat gtcgctttca ccgccaggcg tacgcctgtt ttacgatccg cgcgggcacc    4800
atgccggcgc catcaatgag ctgtgctggg ggctggagga cagggggtc ccctgccaga     4860
ccataaccta tgacggaggc ggtgacgccg ctgcgctggg cgccctggcg ccagaagct     4920
cgcccctgcg ggtgggtatc gggctcagcg cgtccggcga gatagccctc actcatgccc    4980
agctgccggc gacgcgccg ctggctaccg gacacgtcac cgatagcgac gatcaactgc     5040
gtacgctcgg cgccaacgcc gggcagctgg ttaaagtcct gccgttaagt gagagaaact    5100
gaatgtatcg tatctatacc cgcaccgggg ataaaggcac caccgccctg tacggcggca    5160
gccgcatcga gaaagaccat attcgcgtcg aggcctacgg caccgtcgat gaactgatat    5220
cccagctggg cgtctgctac gccacgaccc gcgacgccgg gctgcgggaa agcctgcacc    5280
atattcagca gacgctgttc gtgctggggg ctgaactggc cagcgatgcg cggggcctga    5340
cccgcctgag ccagacgatc ggcgaagagg agataccgc cctggagcgg cttatcgacc     5400
gcaatatggc cgagagcggc ccgttaaaac agttcgtgat cccggggagg aatctcgcct    5460
ctgcccagct gcaccctgat gcttgcgctt gaactggcct agcaaacaca gaaaaaagcc    5520
cgcacctgac agtgcgggct ttttttttcc taggcgatct gtgctgtttg ccacggtatg    5580
cagcaccagc gcgagattat gggctcgcac gctcgactgt cggacggggg cactggaacg    5640
agaagtcagg cgagccgtca cgcccttgac aatgccacat cctgagcaaa taattcaacc    5700
actaaacaaa tcaaccgcgt ttcccggagg taaccaagct tcaccttttg agccgatgaa    5760
caatgaaaag atcaaaacga tttgcagtac tggcccagcg ccccgtcaat caggacgggc    5820
tgattggcga gtggcctgaa gaggggctga tcgccatgga cagcccctt gacccggtct      5880
cttcagtaaa agtggacaac ggtctgatcg tcgaactgga cggcaaacgc cgggaccagt    5940
ttgacatgat cgaccgattt atcgccgatt acgcgatcaa cgttgagcgc acagagcagg    6000
caatgcgcct ggaggcggtg aaatagcccg gtatgctggt ggatattcac gtcagccggg    6060
aggagatcat tgccatcact accgccatca cgccggccaa agcggtcgag gtgatggcgc    6120
agatgaacgt ggtggagatg atgatggcgc tgcagaagat gcgtgcccgc cggacccct     6180
ccaaccagtg ccacgtcacc aatctcaaag ataatccggt gcagattgcc gctgacgccg    6240
ccgaggccgg gatccgcggc ttctcagaac aggagaccac ggtcggtatc gcgcgctacg    6300
cgccgtttaa cgccctggcg ctgttggtcg gttcgcagtg cggccgcccc ggcgtgttga    6360
cgcagtgctc ggtggaagag gccaccgagc tggagctggg catgcgtggc ttaaccagct    6420
acgccgagac ggtgtcggtc tacggcaccg aagcggtatt taccgacggc gatgatacgc    6480
cgtggtcaaa ggcgttcctc gcctcggcct acgcctcccg cgggttgaaa atgcgctaca    6540
cctccggcac cggatccgaa gcgctgatgg gctattcgga gagcaagtcg atgctctacc    6600
tcgaatcgcg ctgcatcttc attactaaag gcgccggggt tcagggactg caaaacggcg    6660
cggtgagctg tatcggcatg accggcgctg tgccgtcggg cattcgggcg gtgctggcgg    6720
aaaacctgat cgcctctatg ctcgacctcg aagtggcgtc cgccaacgac cagactttct    6780
cccactcgga tattcgccgc accgcgcgca ccctgatgca gatgctgccg ggcaccgact    6840
```

-continued

```
ttatttctc cggctacagc gcggtgccga actacgacaa catgttcgcc ggctcgaact    6900
tcgatgcgga agattttgat gattacaaca tcctgcagcg tgacctgatg gttgacggcg    6960
gcctgcgtcc ggtgaccgag gcggaaacca ttgccattcg ccagaaagcg gcgcgggcga    7020
tccaggcggt tttccgcgag ctggggctgc cgccaatcgc cgacgaggag gtggaggccg    7080
ccacctacgc gcacggcagc aacgagatgc gcccgcgtaa cgtggtggag gatctgagtg    7140
cggtggaaga gatgatgaag cgcaacatca ccggcctcga tattgtcggc gcgctgagcc    7200
gcagcggctt tgaggatatc gccagcaata ttctcaatat gctgcgccag cgggtcaccg    7260
gcgattacct gcagacctcg gccattctcg atcggcagtt cgaggtggtg agtgcggtca    7320
acgacatcaa tgactatcag gggccgggca ccggctatcg catctctgcc gaacgctggg    7380
cggagatcaa aaatattccg ggcgtggttc agcccgacac cattgaataa ggcggtattc    7440
ctgtgcaaca gacaacccaa attcagccct cttttaccct gaaaacccgc gagggcgggg    7500
tagcttctgc cgatgaacgc gccgatgaag tggtgatcgg cgtcgccct gccttcgata    7560
aacaccagca tcacactctg atcgatatgc cccatggcgc gatcctcaaa gagctgattg    7620
ccggggtgga agaagagggg cttcacgccc gggtggtgcg cattctgcgc acgtccgacg    7680
tctcctttat ggcctgggat gcggccaacc tgagcggctc ggggatcggc atcggtatcc    7740
agtcgaaggg gaccacggtc atccatcagc gcgatctgct gccgctcagc aacctggagc    7800
tgttctccca ggcgccgctg ctgacgctgg agacctaccg gcagattggc aaaaacgctg    7860
cgcgctatgc gcgcaaagag tcaccttcgc cggtgccggt ggtgaacgat cagatggtgc    7920
ggccgaaatt tatggccaaa gccgcgctat ttcatatcaa agagaccaaa catgtggtgc    7980
aggacgccga gcccgtcacc ctgcacatcg acttagtaag ggagtgacca tgagcgagaa    8040
aaccatgcgc gtgcaggatt atccgttagc cacccgctgc ccggagcata tcctgacgcc    8100
taccggcaaa ccattgaccg atattaccct cgagaaggtg ctctctggcg aggtgggccc    8160
gcaggatgtg cggatctccc gccagaccct tgagtaccag gcgcagattg ccgagcagat    8220
gcagcgccat gcggtggcgc gcaatttccg ccgcgcggcg gagcttatcg ccattcctga    8280
cgagcgcatt ctggctatct ataacgcgct gcgcccgttc cgctcctcgc aggcggagct    8340
gctggcgatc gccgacgagc tggagcacac ctggcatgcg acagtgaatg ccgccttttgt    8400
ccgggagtcg gcggaagtgt atcagcagcg gcataagctg cgtaaaggaa gctaagcgga    8460
ggtcagcatg ccgttaatag ccgggattga tatcggcaac gccaccaccg aggtggcgct    8520
ggcgtccgac tacccgcagg cgagggcgtt tgttgccagc gggatcgtcg cgacgacggg    8580
catgaaaggg acgcgggaca atatcgccgg gaccctcgcc gcgctggagc aggccctggc    8640
gaaaacaccg tggtcgatga gcgatgtctc tcgcatctat cttaacgaag ccgcgccggt    8700
gattggcgat gtggcgatgg agaccatcac cgagaccatt atcaccgaat cgaccatgat    8760
cggtcataac ccgcagacgc cgggcggggt gggcgttggc gtgggacga ctatcgccct    8820
cgggcggctg gcgacgctgc cggcggcgca gtatgccgag gggtggatcg tactgattga    8880
cgacgccgtc gatttccttg acgccgtgtg gtggctcaat gaggcgctcg accggggat    8940
caacgtggtg gcggcgatcc tcaaaaagga cgacggcgtg ctggtgaaca accgcctgcg    9000
taaaaccctg ccggtggtgg atgaagtgac gctgctggag caggtccccg aggggtaat    9060
ggcgcggtg gaagtggccg cgccgggcca ggtggtgcgg atcctgtcga atccctacgg    9120
gatcgccacc ttcttcgggc taagcccgga agagacccag gccatcgtcc ccatcgcccg    9180
cgccctgatt ggcaaccgtt ccgcggtggt gctcaagacc ccgcagggg atgtgcagtc    9240
```

-continued

```
gcgggtgatc ccggcgggca acctctacat tagcggcgaa aagcgccgcg gagaggccga    9300
tgtcgccgag ggcgcggaag ccatcatgca ggcgatgagc gcctgcgctc cggtacgcga    9360
catccgcggc gaaccgggca cccacgccgg cggcatgctt gagcgggtgc gcaaggtaat    9420
ggcgtccctg accggccatg agatgagcgc gatatacatc caggatctgc tggcggtgga    9480
tacgtttatt ccgcgcaagg tgcagggcgg gatgccggc gagtgcgcca tggagaatgc     9540
cgtcgggatg gcggcgatgg tgaaagcgga tcgtctgcaa atgcaggtta tcgcccgcga    9600
actgagcgcc cgactgcaga ccgaggtggt ggtgggcggc gtggaggcca acatggccat    9660
cgccggggcg ttaaccactc ccggctgtgc ggcgccgctg gcgatcctcg acctcggcgc    9720
cggctcgacg gatgcggcga tcgtcaacgc ggaggggcag ataacggcgg tccatctcgc    9780
cggggcgggg aatatggtca gcctgttgat taaaaccgag ctgggcctcg aggatctttc    9840
gctggcggaa gcgataaaaa aatacccgct ggccaaagtg gaaagcctgt tcagtattcg    9900
tcacgagaat ggcgcggtgg agttctttcg ggaagccctc agcccggcgg tgttcgccaa    9960
agtggtgtac atcaaggagg gcgaactggt gccgatcgat aacgccagcc cgctggaaaa   10020
aattcgtctc gtgcgccggc aggcgaaaga gaaagtgttt gtcaccaact gcctgcgcgc   10080
gctgcgccag gtctcacccg gcggttccat tcgcgatatc gcctttgtgg tgctggtggg   10140
cggctcatcg ctggactttg agatcccgca gcttatcacg gaagccttgt cgcactatgg   10200
cgtggtcgcc gggcagggca atattcgggg aacagaaggg ccgcgcaatg cggtcgccac   10260 cggggctgcta ctggccggtc aggcgaatta acgggcgct cgcgccagcc tctaggtaca   10320
aataaaaaag gcacgtcaga tgacgtgcct ttttcttgt ctagcgtgca ccaatgcttc    10380
tggcgtcagg cagccatcgg aagctgtggt atggctgtgc aggtcgtaaa tcactgcata   10440
attcgtgtcg ctcaaggcgc actcccgttc tggataatgt tttttgcgcc gacatcataa   10500
cggttctggc aaatattctg aaatgagctg ttgacaatta atcatccggc tcgtataatg   10560
tgtggaattg tgagcggata acaatttcac acaggaaaca gaccatgact agtaaggagg   10620
acaattccat ggctgctgct gctgatagat taaacttaac ttccggccac ttgaatgctg   10680
gtagaaagag aagttcctct tctgtttctt tgaaggctgc cgaaaagcct ttcaaggtta   10740
ctgtgattgg atctggtaac tggggtacta ctattgccaa ggtggttgcc gaaaattgta   10800
agggataccc agaagttttt gctccaatag tacaaatgtg ggtgttcgaa gaagagatca   10860
atggtgaaaa attgactgaa atcataaata ctagacatca aaacgtgaaa tacttgcctg   10920
gcatcactct acccgacaat ttggttgcta atccagactt gattgattca gtcaaggatg   10980
tcgacatcat cgttttcaac attccacatc aattttttgcc ccgtatctgt agccaattga   11040
aaggtcatgt tgattcacac gtcagagcta tctcctgtct aaagggtttt gaagttggtg   11100
ctaaaggtgt ccaattgcta tcctcttaca tcactgagga actaggtatt caatgtggtg   11160
ctctatctgg tgctaacatt gccaccgaag tcgctcaaga acactggtct gaaacaacag   11220
ttgcttacca cattccaaag gatttcagag gcgagggcaa ggacgtcgac cataaggttc   11280
taaaggcctt gttccacaga ccttacttcc acgttagtgt catcgaagat gttgctggta   11340
tctccatctg tggtgctttg aagaacgttg ttgccttagg ttgtgttttc gtcgaaggtc   11400
taggctgggg taacaacgct tctgctgcca tccaaagagt cggtttgggt gagatcatca   11460
gattcggtca aatgttttc ccagaatcta gagaagaaac atactaccaa gagtctctg    11520 gtgttgctga tttgatcacc acctgcgctg gtggtagaaa cgtcaaggtt gctaggctaa   11580
```

```
tggctacttc tggtaaggac gcctgggaat gtgaaaagga gttgttgaat ggccaatccg    11640
ctcaaggttt aattacctgc aaagaagttc acgaatggtt ggaaacatgt ggctctgtcg    11700
aagacttccc attatttgaa gccgtatacc aaatcgttta caacaactac ccaatgaaga    11760
acctgccgga catgattgaa gaattagatc tacatgaaga ttagatttat tggatccagg    11820
aaacagacta gaattatggg attgactact aaacctctat ctttgaaagt taacgccgct    11880
ttgttcgacg tcgacggtac cattatcatc tctcaaccag ccattgctgc attctggagg    11940
gatttcggta aggacaaacc ttatttcgat gctgaacacg ttatccaagt ctcgcatggt    12000
tggagaacgt ttgatgccat tgctaagttc gctccagact ttgccaatga agagtatgtt    12060
aacaaattag aagctgaaat tccggtcaag tacggtgaaa aatccattga agtcccaggt    12120
gcagttaagc tgtgcaacgc tttgaacgct ctaccaaaag agaaatgggc tgtggcaact    12180
tccggtaccc gtgatatggc acaaaaatgg ttcgagcatc tgggaatcag gagaccaaag    12240
tacttcatta ccgctaatga tgtcaaacag ggtaagcctc atccagaacc atatctgaag    12300
ggcaggaatg gcttaggata tccgatcaat gagcaagacc cttccaaatc taaggtagta    12360
gtatttgaag acgctccagc aggtattgcc gccggaaaag ccgccggttg taagatcatt    12420
ggtattgcca ctactttcga cttggacttc ctaaaggaaa aaggctgtga catcattgtc    12480
aaaaaccacg aatccatcag agttggcggc tacaatgccg aaacagacga agttgaattc    12540
atttttgacg actacttata tgctaaggac gatctgttga aatggtaacc cgggctgcag    12600
gcatgcaagc ttggctgttt tggcggatga gagaagattt tcagcctgat acagattaaa    12660
tcagaacgca gaagcggtct gataaaacag aatttgcctg gcggcagtag cgcggtggtc    12720
ccacctgacc ccatgccgaa ctcagaagtg aaacgccgta gcgccgatgg tagtgtgggg    12780
tctccccatg cgagagtagg gaactgccag gcatcaaata aaacgaaagg ctcagtcgaa    12840
agactgggcc tttcgtttta tctgttgttt gtcggtgaac gctctcctga gtaggacaaa    12900
tccgccggga gcggatttga acgttgcgaa gcaacggccc ggagggtggc gggcaggacg    12960
cccgccataa actgccaggc atcaaattaa gcagaaggcc atcctgacgg atggcctttt    13020
tgcgtttcta caaactccag ctggatcggg cgctagagta tacatttaaa tggtaccctc    13080
tagtcaaggc cttaagtgag tcgtattacg gactggccgt cgttttacaa cgtcgtgact    13140
gggaaaaccc tggcgttacc caacttaatc gccttgcagc acatccccct ttcgccagct    13200
ggcgtaatag cgaagaggcc cgcaccgatc gcccttccca acagttgcgc agcctgaatg    13260
gcgaatggcg cctgatgcgg tatttctccc ttacgcatct gtgcggtatt tcacaccgca    13320
tatggtgcac tctcagtaca atctgctctg atgccgcata gttaagccag ccccgacacc    13380
cgccaacacc cgctgacgag ct                                            13402
```

<210> SEQ ID NO 2
<211> LENGTH: 34
<212> TYPE: DNA
<213> ORGANISM: artificial sequence
<220> FEATURE:
<223> OTHER INFORMATION: primer

<400> SEQUENCE: 2
ttcgagctca tgtctaaatt atatggcagc atcg                              34

<210> SEQ ID NO 3
<211> LENGTH: 35
<212> TYPE: DNA
<213> ORGANISM: artificial sequence -continued

```
<220> FEATURE:
<223> OTHER INFORMATION: primer

<400> SEQUENCE: 3
accttaatta attaagcggc tgctatcttt ttagc                              35

<210> SEQ ID NO 4
<211> LENGTH: 78
<212> TYPE: DNA
<213> ORGANISM: artificial sequence
<220> FEATURE:
<223> OTHER INFORMATION: multiple cloning site

<400> SEQUENCE: 4
ggcgcgccgc tagcttaatt aacggaccga tgcatgagct cacgcgtgtt taaacaccgg    60
tgctcttcga tctacgta                                                  78

<210> SEQ ID NO 5
<211> LENGTH: 55
<212> TYPE: DNA
<213> ORGANISM: artificial sequence
<220> FEATURE:
<223> OTHER INFORMATION: terminator

<400> SEQUENCE: 5
aacatatctc tgagaccgcg atgccgcctg gcgtcgcggt ttgtttttca tctct         55

<210> SEQ ID NO 6
<211> LENGTH: 55
<212> TYPE: DNA
<213> ORGANISM: artificial sequence
<220> FEATURE:
<223> OTHER INFORMATION: terminator

<400> SEQUENCE: 6
agcacgcagt caaacataaa acccgcgcca ttgcgcgggt tttttatgc ccgaa          55

<210> SEQ ID NO 7
<211> LENGTH: 32
<212> TYPE: DNA
<213> ORGANISM: artificial sequence
<220> FEATURE:
<223> OTHER INFORMATION: primer

<400> SEQUENCE: 7
tccgagctca tgatcctgtg ttgtggtgaa gc                                  32

<210> SEQ ID NO 8
<211> LENGTH: 34
<212> TYPE: DNA
<213> ORGANISM: artificial sequence
<220> FEATURE:
<223> OTHER INFORMATION: primer

<400> SEQUENCE: 8
accttaatta atcacaaacc gatttcatgc gcga                                34

<210> SEQ ID NO 9
<211> LENGTH: 100
<212> TYPE: DNA
<213> ORGANISM: artificial sequence
<220> FEATURE:
<223> OTHER INFORMATION: primer

<400> SEQUENCE: 9
```

-continued

```
gtgggttatc gctcgattga taccgccgcg gcctacaaga acgaagaagg tgtcggcaaa        60
gccctgaaaa atgcctcatg tgtaggctgg agctgcttcg                             100
```

<210> SEQ ID NO 10
<211> LENGTH: 100
<212> TYPE: DNA
<213> ORGANISM: artificial sequence
<220> FEATURE:
<223> OTHER INFORMATION: primer

<400> SEQUENCE: 10

```
ttagccgccg aactggtcag gatcgggacc gagacgcttg ccctgatcga gttttgcaat        60
ttcgccgagt tcgtctttgt catatgaata tcctccttag                             100
```

<210> SEQ ID NO 11
<211> LENGTH: 23
<212> TYPE: DNA
<213> ORGANISM: artificial sequence
<220> FEATURE:
<223> OTHER INFORMATION: primer

<400> SEQUENCE: 11

```
ccgcaacccg caatttcttt gag                                                23
```

<210> SEQ ID NO 12
<211> LENGTH: 31
<212> TYPE: DNA
<213> ORGANISM: artificial sequence
<220> FEATURE:
<223> OTHER INFORMATION: primer

<400> SEQUENCE: 12

```
gatgccgctg gcgattcagg ttcatcatgc c                                       31
```

<210> SEQ ID NO 13
<211> LENGTH: 31
<212> TYPE: DNA
<213> ORGANISM: artificial sequence
<220> FEATURE:
<223> OTHER INFORMATION: primer

<400> SEQUENCE: 13

```
gcctcaaaat gttctttacg atgccattgg g                                       31
```

<210> SEQ ID NO 14
<211> LENGTH: 23
<212> TYPE: DNA
<213> ORGANISM: artificial sequence
<220> FEATURE:
<223> OTHER INFORMATION: primer

<400> SEQUENCE: 14

```
cgtcagtttg ggttatcgca acg                                                23
```

UTILIZATION OF FRUCTOSE IN MICROBIAL PRODUCTION STRAINS

FIELD OF INVENTION

This invention comprises a method for the utilization of fructose and mixed feeds containing fructose by a microorganism as a nutrient supply for production of substances such as cell mass, glycerol, and 1,3-propanediol.

BACKGROUND

Many commercially useful microorganisms use glucose as their main carbohydrate source. The use of glucose by microorganisms developed for production of commercially desirable products does not generally provide a commercially desirable method for production due to the high cost of glucose. The use of fructose and mixed feedstocks containing fructose and other sugars as carbohydrate sources for microorganism production systems would be more commercially desirable, because these materials are more readily available at a lower cost. Desirable commercial feedstocks contain non-glucose breakdown products of starch or a variety of sugars such as fructose and xylose. Low cost feedstock derived from sucrose generally contains essentially equal amounts of glucose and fructose. Use of the fructose present in these types of feedstocks is desirable to obtain efficient production using a microorganism, such as in fermentation. However, microorganisms used to develop production microorganisms for making commercially desirable products do not generally have the ability to efficiently utilize fructose as a major carbohydrate source.

Though the most common sugar transport system found in prokaryotes, the phosphoenolpyruvate-dependent phosphotransferase system (PTS), is able to transport fructose, glucose is the preferred substrate. The PTS has been shown to mediate the efficient use of sugars through sensing and adjusting to sugar gradients and regulating expression of genes encoding enzymes responsible for uptake and metabolism of the various substrates (Stülke, J., and W. Hillen. 1999. Curr. Opin. Microbiol. 2:195-201; Mechanism and Regulation of Carbohydrate Transport in Bacteria, 1985, Academic Press, New York, M. H. Saiered., pp 70-74; Jacob, F. and J. Monod, 1961, J. Mol. Biol. 3:318-356). Bacterial cells show preferential sugar use, with glucose being most desirable. In artificial media containing every PTS sugar, glucose is metabolized to its entirety ahead of all other sugars (McGuinnis, J. F. and Palgen, K. 1969, J. Bacteriol. 100:902-913). Bacterial cells are adapted to recovering maximal energy from a substrate, and glucose provides slightly more energy compared to many other sugars, thus supporting a higher specific growth rate (Juana M. Gancedo, Microbiol Mol Biol Rev., 1998, 62:334-361).

In the PTS, sugars are phosphorylated during transport, and this activity is directly linked to the internal concentration of a glycolytic intermediate, phosphoenolpyruvate (PEP). PEP is the source for phosphate used to create a high-energy ester linkage that is necessary for subsequent sugar metabolism. The linkage of sugar transport and PEP limits the availability of PEP for use in synthesis of other products which are derived from PEP. For example, the yield of aromatic compounds produced by fermentation using $E.\ coli$ is limited by the availability of PEP (Flores, N., Xiao, J., Berry, A., Bolivar, F. and F. Valle, 1996 Nat. Biotechnol. 14:620-623). Eliminating glucose uptake by PTS removes the connection between PEP and transport, making PEP available to biosynthetic pathways involved in the production of aromatics. Making use of an alternative (non-PTS) glucose transport system was demonstrated to be an effective method of increasing PEP levels and yield of compounds which use PEP as a precursor such as phenylalanine (Chen, R., Hatzimanikatis, V., Yap, W., Postma, P. and J. E. Bailey 1997, Biotechnol. Prog. 13:768-775).

Bypassing the PTS also conserves a molecule of ATP. Production strains of microorganisms have been developed which lack PTS and provide an alternative glucose assimilation system. In WO 2004/033471, a $PTS^-/Glu^-$ (non glucose utilizing) bacterial host cell was converted to glucose utilizing capability by increasing the expression of an endogenous glucose assimilation protein. Specifically, a promoter with the ability to direct high expression was integrated into the genome adjacent to a galactose-proton symporter (galP) coding region. In addition, in this galP-engineered strain, a high expression promoter was integrated adjacent to a coding region for glucose kinase to provide enhanced glucose utilizing capability. In this report, it is suggested that other glucose phosphorylating enzymes may be overexpressed to provide enhanced glucose utilization. Fructokinases are mentioned as possibilities since these are inferred as having some glucose phosphorylating activity, but there is no mention of using fructose as a substrate.

In U.S. Published Patent Application No. 2001/0049126, strains of $Escherichia$ that are not able to utilize sucrose were provided that capability by adding sucrose PTS genes or sucrose non-PTS genes. The introduction of these genes provided the recipient $E.\ coli$ strain with the capability of growing on sucrose and producing the amino acid threonine. Different strains that had been engineered for production of various amino acids and that expressed the sucrose non-PTS genes were able to produce these amino acids when grown on sucrose.

In WO 98/18937, production of substances that use PEP as a precursor was improved by freeing PEP from use in phosphorylation during transport. PEP derivatives that are substances from aromatic metabolism are the products which this report addresses, specifically aromatic amino acids. Increased expression of glucokinase in a $PTS^+$ strain of $E.\ coli$ or of glucokinase and the $Zymomonas\ mobilis$ glucose facilitator (glf) protein in a $PTS^-$ $E.\ coli$ strain resulted in increased production of the amino acid phenylalanine with growth on glucose medium.

In Weisser et al. (1995, J. Bacteriol. 177:3351-3354), induced expression of fructokinase (frk) and glf in a $PTS^-$ $E.\ coli$ strain did not support sustained growth of the cells on fructose. These cells that were engineered for high expression of the $Zymomonas\ mobilis$ glf gene and the $Zymomonas\ mobilis$ frk gene, doubled once and then stopped growing and eventually lysed. The authors speculate that a metabolic imbalance, such as accumulation of fructose-6-phosphate or draining of ATP, could be the reason for the inability to grow.

In U.S. Published Patent Application No. 2004/0152174A1, $E.\ coli$ strains were engineered to produce high yields of 1,3-propanediol, using glucose as the carbon substrate. Suggestions of further suitable carbon substrates include lactose, sucrose, and fructose. However, fructokinase is not present in this disclosure.

Thus, the gene expression requirements for efficient fructose utilization in a $PTS^-$ microbial production host remain an unsolved issue. As described above, it is desirable to provide fructose utilization capability to $PTS^-$ microorganisms for growth on fructose during production of commercial products, because of the availability and lower cost of fructose-containing carbohydrate sources.

SUMMARY OF THE INVENTION

The present invention provides a process for the enhanced utilization of fructose by a PTS⁻ microorganism. Specifically, fructose is used as a carbohydrate source in the production of glycerol and products that are derived from glycerol. In one embodiment, a PTS⁻ microorganism expresses increased fructokinase (Frk) activity to increase the efficiency of fructose metabolism for production of microbial products. In a second embodiment, a PTS⁻ microorganism expresses increased fructokinase (Frk) activity and galactose-proton symporter (GalP) activity to increase efficiency of fructose uptake and metabolism for production of microbial products. In a third embodiment, a PTS⁻ microorganism expresses increased fructokinase (Frk) activity and galactose-proton symporter (GalP) activity, and in addition has a disrupted yqhE gene, thereby further enhancing production of microbial products. In a fourth embodiment a PTS⁻ microorganism expresses GalP and Frk activities, and includes genetic modifications for 1,3-propanediol synthesis, and thereby shows enhanced use of fructose to produce 1,3-propanediol.

Accordingly the invention provides a process for the bioproduction of microbial products comprising:
 (a) providing a PTS⁻ microorganism expressing an endogenous fructose transport protein activity;
 (b) expressing increased fructokinase activity in the microorganism of step (a);
 (c) culturing the microorganism of (b) in a fructose-containing medium, whereby the microorganism utilizes fructose to produce microbial products; and
 (d) optionally, recovering at least one microbial product.

In addition, the process described optionally comprises a disruption of an endogenous yqhE gene and/or expression of increased fructose transport protein activity.

Another aspect is for a process for the bioproduction of microbial products comprising:
 (a) providing a PTS⁻ microorganism;
 (b) expressing increased fructokinase activity in the microorganism of step (a);
 (c) expressing increased fructose transport protein activity in the microorganism of step (b);
 (d) culturing the microorganism of (c) in a fructose-containing medium for at least two generations, whereby the microorganism utilizes fructose to produce microbial products; and
 (e) optionally, recovering at least one microbial product.

In an alternate embodiment the invention provides a PTS⁻ *Escherichia coli* comprising an increased fructokinase activity, wherein the PTS⁻ *Escherichia coli* expresses an endogenous fructose transport protein activity. In addition, the *E. coli* optionally comprises a disrupted yqhE gene and/or increased fructose transport protein activity, with a preferred level of fructokinase activity that is greater than 0.62 U/mg.

BRIEF SEQUENCE DESCRIPTIONS

The following sequences conform with 37 C.F.R. §§ 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO:1 is the nucleotide sequence for the pSYCO109 plasmid.

SEQ ID NOs:2-3 are oligonucleotide primers used to amplify the scrK coding region from *Streptococcus mutans*.

SEQ ID NO:4 is the multiple cloning site sequence for the pSYCO400 vector.

SEQ ID NO:5 is the LexA terminator sequence.

SEQ ID NO:6 is the LeuA terminator sequence.

SEQ ID NOs:7-8 are oligonucleotide primers used to amplify the scrK coding region from *Agrobacterium tumefaciens*.

SEQ ID NOs:9-10 are oligonucleotide primers yqhEFRTF and yqhEFRTR, respectively, used to amplify the yqhE gene deletion cassette.

SEQ ID NOs:11-12 are oligonucleotide primers yqh6800F and vec5, respectively, used to amplify a 5' yqh/CmR fragment to confirm deletion.

SEQ ID NOs:13-14 are oligonucleotide primers vec6 and yqh8419R, respectively, used to amplify a 3' yqh/CmR fragment to confirm deletion.

DETAILED DESCRIPTION OF THE INVENTION

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The present invention provides a process for enhanced utilization of fructose as an energy source by a PTS⁻ microorganism. The process includes expressing increased fructokinase activity in a PTS⁻ microorganism. To further enhance fructose utilization, a galactose-proton symporter is also expressed in the PTS⁻ microorganism expressing increased fructokinase activity. An additional enancement in fructose utilization is obtained by disrupting the endogenous yqhE gene in the PTS⁻ microorganism expressing increased fructokinase activity and, optionally, a galactose-proton symporter. Fructose is used as a carbon source for the production of microbial products. Microbial production of glycerol and glycerol derivatives is of particular interest. Specifically, through the process of the invention, fructose is utilized by a production host strain that has been engineered for high production of the glycerol derivative 1,3-propanediol. The present invention also provides a production host which utilizes fructose as a carbohydrate source for the production of glycerol and glycerol derivatives, such as 1,3-propanediol.

Terms And Definitions

The invention can be more fully understood with reference to the following terms and definitions used in the claims and specifications.

The term "fructokinase" refers to a protein that has the ability to catalyse the conversion of D-fructose+ATP to fructose-phosphate+ADP. Typical of fructokinase is EC 2.7.1.4. Enzymes that have some ability to phosphorylate fructose, whether or not this activity is their predominant activity, may be referred to as a fructokinase. Abbreviations used for genes encoding fructokinases and proteins having fructokinase activity include, for example, "Frk", "scrK", "cscK", "FK", and "KHK". Fructokinase is encoded by the scrK gene in *Agrobacterium* and *Streptococcus*.

The term "fructokinase activity" refers to an enzymatic activity resulting in the phosphorylation of fructose, thereby providing fructose-phosphate. Fructokinase activity is found, for example, in kinases designated as EC 2.7.1.4, as well as in various hexose kinases (EC 2.7.1.3 and EC 2.7.1.1).

The term "increased fructokinase activity" refers to a fructokinase activity level which is higher than the naturally occurring level for the host microorganism.

The term "fructose transport protein activity" refers to a protein activity which enables the movement of fructose into a microorganism cell. This activity may be provided by a protein whose well-known function is to transport a different sugar, but which is also able to support the transport of fructose.

The term "glycerol derivative" refers to a compound that is synthesized using glycerol or in a pathway that includes glycerol. Examples of such products include 3-hydroxypropionic acid (3-HPA), methylglyoxal, 1,2-propanediol, and 1,3-propanediol.

The term "microbial product" refers to a subtance that is produced as a result of the metabolism of a microorganism. The substance may be naturally produced by the microorganism, or the microorganism may be engineered to produce the substance.

The term "YqhE" refers to a protein that catalyzes the NAD(P)H dependent reduction of keto-esters. A typical ketoreductase is encoded by the yqhE gene of *E. coli* (GenBank®, Accession # U00096).

The terms "phosphocarrier protein HPr" and "PtsH" refer to the phosphocarrier protein encoded by ptsH in *E. coli*. The terms "phosphoenolpyruvate-protein phosphotransferase" and "PtsI" refer to the phosphotransferase, EC 2.7.3.9, encoded by ptsI in *E. coli*. The terms "glucose-specific IIA component", and "Crr" refer to EC 2.7.1.69, encoded by crr in *E. coli*. PtsH, PtsI, and Crr comprise the PTS system.

The term "phosphoenolpyruvate-sugar phosphotransferase system", "PTS system", or "PTS" refers to the phosphoenolpyruvate-dependent sugar uptake system.

The terms "aldehyde dehydrogenase A" and "AldA" refer to a protein that catalyzes the conversion of $H_2O+NAD^++$ aldehyde to NADH+alcohol. Typical of aldehyde dehydrogenase A is EC 1.2.1.22. Aldehyde dehydrogenase A is encoded by aldA in *E. coli*.

The terms "aldehyde dehydrogenase B" and "AldB" refer to a protein that catalyzes the conversion of $H_2O+NAD^++$ aldehyde to NADH+alcohol. Typical of aldehyde dehydrogenase B is EC 1.2.1.22. Aldehyde dehydrogenase B is encoded by aldB in *E. coli*.

The terms "galactose-proton symporter" and "GalP" refer to a protein that catalyses the transport of a sugar and a proton from the periplasm to the cytoplasm. D-glucose is a preferred substrate for GalP, but other sugars including fructose are also substrates. Galactose-proton symporter is encoded by galP in *E. coli*.

The terms "glucokinase" and "Glk" refer to a protein that catalyses the conversion of D-glucose+ATP to glucose-6-phosphate+ADP. Typical of glucokinase is EC 2.7.1.2. Glucokinase is encoded by glk in *E. coli*.

The terms "phosphoenolpyruvate carboxylase" and "Ppc" refer to a protein that catalyses the conversion of phosphoenolpyruvate+$H_2O$+$CO_2$ to phosphate+oxaloacetic acid. Typical of phosphoenolpyruvate carboxylase is EC 4.1.1.31. Phosphoenolpyruvate carboxylase is encoded by ppc in *E. coli*.

The terms "glyceraldehyde 3-phosphate dehydrogenase" and "GapA" refer to a protein that catalyses the conversion of glyceraldehyde-3-phosphate+phosphate+$NAD^+$ to 3-phospho-D-glyceroyl-phosphate+NADH+$H^+$. Typical of glyceraldehyde 3-phosphate dehydrogenase is EC 1.2.1.12. Glyceraldehyde 3-phosphate dehydrogenase is encoded by gapA in *E. coli*.

The terms "NADH dehydrogenase II", "NDH II" and "Ndh" refer to the type II NADH dehydrogenase, a protein that catalyzes the conversion of ubiquinone-8+NADH+$H^+$ to ubiquinol-8+$NAD^+$. Typical of NADH dehydrogenase II is EC 1.6.99.3. NADH dehydrogenase II is encoded by ndh in *E. coli*.

The terms "aerobic respiration control protein" and "ArcA" refer to a global regulatory protein. The aerobic respiration control protein is encoded by arcA in *E. coli*.

The terms "methylglyoxal synthase" and "MgsA" refer to a protein that catalyzes the conversion of dihydroxyacetone phosphate to methyl-glyoxal+phosphate. Typical of methylglyoxal synthase is EC 4.2.3.3. Methylglyoxal synthase is encoded by mgsA in *E. coli*.

The terms "phosphogluconate dehydratase" and "Edd" refer to a protein that catalyzed the conversion of 6-phosphogluconate to 2-keto-3-deoxy-6-phospho-gluconate+$H_2O$. Typical of phosphogluconate dehydratase is EC 4.2.1.12. Phosphogluconate dehydratase is encoded by edd in *E. coli*.

The term "YciK" refers to a putative enzyme encoded by yciK which is translationally coupled to btuR, the gene encoding Cob(I)alamin adenosyltransferase in *E. coli*.

The term "cob(I)alamin adenosyltransferase" refers to an enzyme responsible for the transfer of a deoxyadenosyl moiety from ATP to the reduced corrinoid. Typical of cob(I) alamin adenosyltransferase is EC 2.5.1.17. Cob(I)alamin adenosyltransferase is encoded by the gene "btuR" (GenBank® M21528) in *E. coli*, "cobA" (GenBank® L08890) in *Salmonella typhimurium*, and "cobO" (GenBank® M62866) in *Pseudomonas denitrificans*.

The term "non-specific catalytic activity" refers to the polypeptide(s) responsible for an enzyme activity that is sufficient to catalyze the interconversion of 3-HPA and 1,3-propanediol and specifically excludes 1,3-propanediol oxidoreductase(s). Typically these enzymes are alcohol dehydrogenases. Such enzymes may utilize cofactors other than $NAD^+$/NADH, including but not limited to flavins such as FAD or FMN. A gene for a non-specific alcohol dehydrogenase (yqhD) is found, for example, to be endogenously encoded and functionally expressed within *E. coli* $K_{12}$ strains.

The term "1.6 long GI promoter" refers to a DNA fragment containing a promoter from the *Streptomyces lividans* glucose isomerase gene as described in U.S. patent application Ser. No. 10/420587. This promoter fragment includes a mutation which decreases its activity as compared to the wild type *Streptomyces lividans* glucose isomerase gene promoter.

The terms "glycerol-3-phosphate dehydrogenase" and "G3PDH" refer to a polypeptide responsible for an enzyme activity that catalyzes the conversion of dihydroxyacetone phosphate (DHAP) to glycerol-3-phosphate (G3P). In vivo G3PDH may be NADH, NADPH, or FAD-dependent. When specifically referring to a cofactor specific glycerol-3-phosphate dehydrogenase, the terms "NADH-dependent glycerol-3-phosphate dehydrogenase", "NADPH-dependent glycerol-3-phosphate dehydrogenase" and "FAD-dependent glycerol-3-phosphate dehydrogenase" are used. As it is generally the case that NADH-dependent and NADPH-dependent glycerol-3-phosphate dehydrogenases are able to use NADH and NADPH interchangeably (for example by the gene encoded by gpsA), the terms NADH-dependent and NADPH-dependent glycerol-3-phosphate dehydrogenase are used interchangeably. The NADH-dependent enzyme (EC 1.1.1.8) is encoded by several genes including, for example, GPD1 (GenBank® Z74071x2), GPD2 (GenBank® Z35169x1), GPD3 (GenBank® G984182), and DAR1 (GenBank® Z74071x2). The NADPH-dependent enzyme (EC 1.1.1.94) is encoded, for example, by gpsA (GenBank® U321643, (cds 197911-196892) G466746 and L45246). The FAD-dependent enzyme (EC 1.1.99.5) is encoded, for example, by GUT2 (GenBank® Z47047x23), glpD (GenBank® G147838), or glpABC (GenBank® M20938) (see WO 99/28480 and references therein, which are herein incorporated by reference).

The terms "glycerol-3-phosphatase", "sn-glycerol-3-phosphatase", or "d,l-glycerol phosphatase", and "G3P phosphatase" refer to a polypeptide responsible for an enzyme activity that catalyzes the conversion of glycerol-3-phosphate and water to glycerol and inorganic phosphate. G3P phosphatase is encoded, for example, by GPP1 (GenBank® Z47047x125), or GPP2 (GenBank® U18813x11) (see WO 99/28480 and references therein, which are herein incorporated by reference).

The term "glycerol kinase" refers to a polypeptide responsible for an enzyme activity that catalyzes the conversion of glycerol and ATP to glycerol-3-phosphate and ADP. The high-energy phosphate donor ATP may be replaced by physiological substitutes (e.g., phosphoenolpyruvate). Glycerol kinase is encoded, for example, by GUT1 (GenBank® U11583x19) and glpK (GenBank® L19201) (see WO 99/28480 and references therein, which are herein incorporated by reference).

The term "glycerol dehydrogenase" refers to a polypeptide responsible for an enzyme activity that catalyzes the conversion of glycerol to dihydroxyacetone (E.C. 1.1.1.6) or glycerol to glyceraldehyde (E.C. 1.1.1.72). A polypeptide responsible for an enzyme activity that catalyzes the conversion of glycerol to dihydroxyacetone is also referred to as a "dihydroxyacetone reductase". Glycerol dehydrogenase may be dependent upon NADH (E.C. 1.1.1.6), NADPH (E.C. 1.1.1.72), or other cofactors (e.g., E.C. 1.1.99.22). A NADH-dependent glycerol dehydrogenase is encoded, for example, by gidA (GenBank® U00006) (see WO 9928480 and references therein, which are herein incorporated by reference).

The term "dehydratase enzyme" or "dehydratase" will refer to any enzyme activity that catalyzes the conversion of a glycerol molecule to the product 3-hydroxypropionaldehyde. The dehydratase enzymes referred to herein include a glycerol dehydratase (E.C. 4.2.1.30) and a diol dehydratase (E.C. 4.2.1.28) having preferred substrates of glycerol and 1,2-propanediol, respectively. Genes for dehydratase enzymes have been identified in *Klebsiella pneumoniae, Citrobacter freundii, Clostridium pasteurianum, Salmonella typhimurium*, and *Klebsiella oxytoca*. In each case, the dehydratase is composed of three subunits: the large or "α" subunit, the medium or "β" subunit, and the small or "γ" subunit. The genes are also described in, for example, Daniel et al. (*FEMS Microbiol. Rev.* 22, 553 (1999)) and Toraya and Mori (*J. Biol. Chem.* 274, 3372 (1999)). Genes encoding the large or "α" subunit of glycerol dehydratase include, for example, dhaB1, gldA and dhaB; genes encoding the medium or "β" subunit include, for example, dhaB2, gldB, and dhaC; genes encoding the small or "γ" subunit include, for example, dhaB3, gldC, and dhaE. Genes encoding the large or "α" subunit of diol dehydratase include, for example, pduC and pddA; genes encoding the medium or "β" subunit include, for example, pduD and pddB; genes encoding the small or "γ" subunit include, for example, pduE and pddC.

Glycerol and diol dehydratases are subject to mechanism-based suicide inactivation by glycerol and some other substrates (Daniel et al., *FEMS Microbiol. Rev.* 22, 553 (1999)). The term "dehydratase reactivation factor" refers to those proteins responsible for reactivating the dehydratase activity. The terms "dehydratase reactivating activity", "reactivating the dehydratase activity" or "regenerating the dehydratase activity" refers to the phenomenon of converting a dehydratase not capable of catalysis of a substrate to one capable of catalysis of a substrate or to the phenomenon of inhibiting the inactivation of a dehydratase or the phenomenon of extending the useful half-life of the dehydratase enzyme in vivo. Two proteins have been identified as being involved as the dehydratase reactivation factor (see, e.g., WO 98/21341 (U.S. Pat. No. 6,013,494) and references therein, which are herein incorporated by reference; Daniel et al., supra; Toraya and Mori, *J. Biol. Chem.* 274. 3372 (1999); and Tobimatsu et al. *J. Bacteriol.* 181, 4110 (1999)). Genes encoding one of the proteins include, for example, orfZ, dhaB4, gdrA, pduG and ddrA. Genes encoding the second of the two proteins include, for example, orfX, orf2b, gdrB, pduH and ddrB.

The terms "1,3-propanediol oxidoreductase", "1,3-propanediol dehydrogenase" or "DhaT" refer to the polypeptide (s) responsible for an enzyme activity that is capable of catalyzing the interconversion of 3-HPA and 1,3-propanediol provided the gene(s) encoding such activity is found to be physically or transcriptionally linked to a dehydratase enzyme in its natural (i.e., wild type) setting; for example, the gene is found within a dha regulon as is the case with dhaT from *Klebsiella pneumoniae*. Genes encoding a 1,3-propanediol oxidoreductase include, for example, dhaT from *Klebsiella pneumoniae, Citrobacter freundii,* and *Clostridium pasteurianum*. Each of these genes encode a polypeptide belonging to the family of type III alcohol dehydrogenases, which exhibits a conserved iron-binding motif, and has a preference for the NAD$^+$/NADH linked interconversion of 3-HPA and 1,3-propanediol (Johnson and Lin, *J. Bacteriol.* 169, 2050 (1987); Daniel et al., *J. Bacteriol.* 177, 2151 (1995); and Leurs et al., *FEMS Microbiol. Lett.* 154, 337 (1997)). Enzymes with similar physical properties have been isolated from *Lactobacillus brevis* and *Lactobacillus buchneri* (Veiga da Dunha and Foster, *Appl. Environ. Microbiol.* 58, 2005 (1992)).

The term "dha regulon" refers to a set of associated genes or open reading frames encoding various biological activities, including but not limited to a dehydratase activity, a reactivation activity, and a 1,3-propanediol oxidoreductase. Typically a dha regulon comprises the open reading frames dhaR, orfy, dhaT, orfX, orfW, dhaB1, dhaB2, dhaB3, and orfZ as described in U.S. Published Patent Application No. 2004/0152174.

The terms "function" or "enzyme function" refer to the catalytic activity of an enzyme in altering the energy required to perform a specific chemical reaction. It is understood that such an activity may apply to a reaction in equilibrium where the production of either product or substrate may be accomplished under suitable conditions.

The terms "polypeptide" and "protein" are used interchangeably.

The terms "carbon substrate" and "carbon source" refer to a carbon source capable of being metabolized by host microorganisms of the present invention and particularly carbon sources selected from the group consisting of monosaccharides, oligosaccharides, and polysaccharides, or mixtures thereof.

The term "fructose-containing medium" refers to a substance used to support the growth of microorganism cells that includes fructose. Fructose is used as a carbon source by the microorganisms. This medium may contain additional carbon sources, such as other sugars.

The term "mixed sugar feed" refers to a solution that contains multiple types of sugars which is introduced into a microorganism culture as a carbon source.

The terms "host cell" or "host microorganism" refer to a microorganism capable of receiving foreign or heterologous genes and of expressing those genes to produce an active gene product.

The terms "transformation" and "transfection" refer to the acquisition of new genes or other genetic material, such as a promoter, in a cell after the incorporation of nucleic acid. The acquired genes/genetic material may be integrated into chromosomal DNA or introduced as extrachromosomal replicating sequences. The term "transformant" refers to the product of a transformation.

The term "genetically altered" refers to the process of changing hereditary material by transformation or mutation.

The terms "recombinant microorganism" and "transformed host" refer to any microorganism having been transformed with heterologous or foreign genes or extra copies of homologous genes.

"Gene" refers to a nucleic acid fragment that expresses a specific protein. It may or may not include regulatory sequences preceding (5' non-coding sequences) and following (3' non-coding sequences) the coding sequence. "Native gene" and "wild-type gene" refer to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" or "heterologous" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

The terms "foreign DNA" and "heterologous DNA" refer to DNA not normally found in the host organism, but that is introduced into the host organism by gene transfer.

The terms "encoding" and "coding" refer to the process by which a gene, through the mechanisms of transcription and translation, produces an amino acid sequence. It is understood that the process of encoding a specific amino acid sequence includes DNA sequences that may involve base changes that do not cause a change in the encoded amino acid, or which involve base changes which may alter one or more amino acids, but do not affect the functional properties of the protein encoded by the DNA sequence. It is therefore understood that the invention encompasses more than the specific exemplary sequences.

The term "isolated" refers to a protein or DNA sequence that is removed from at least one component with which it is naturally associated.

An "isolated nucleic acid molecule" is a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

"Substantially similar" refers to nucleic acid molecules wherein changes in one or more nucleotide bases result in substitution of one or more amino acids, but do not affect the functional properties of the protein encoded by the DNA sequence. "Substantially similar" also refers to nucleic acid molecules wherein changes in one or more nucleotide bases do not affect the ability of the nucleic acid molecule to mediate alteration of gene expression by antisense or co-suppression technology. "Substantially similar" also refers to modifications of nucleic acid molecules (such as deletion or insertion of one or more nucleotide bases) that do not substantially affect the functional properties of the resulting transcript vis-à-vis the ability to mediate alteration of gene expression by antisense or co-suppression technology or alteration of the functional properties of the resulting protein molecule. The invention encompasses more than the specific exemplary sequences.

For example, alterations in the gene sequence which reflect the degeneracy of the genetic code are contemplated. Also, it is well known in the art that alterations in a gene which result in the production of a chemically equivalent amino acid at a given site, but do not effect the functional properties of the encoded protein are common. Substitutions are defined for the discussion herein as exchanges within one of the following five groups:

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, Trp.

Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product.

In many cases, nucleotide changes which result in alteration of the N-terminal and C-terminal portions of the protein molecule would also not be expected to alter the activity of the protein.

Each of the proposed modifications is well within the routine skill in the art, as is determination of retention of biological activity of the encoded products. Moreover, the skilled artisan recognizes that substantially similar sequences encompassed by this invention are also defined by their ability to hybridize, under stringent conditions (0.1×SSC, 0.1% SDS, 65° C. and washed with 2×SSC, 0.1% SDS followed by 0.1×SSC, 0.1% SDS), with the sequences exemplified herein. Preferred substantially similar nucleic acid fragments of the instant invention are those nucleic acid fragments whose DNA sequences are at least 80% identical to the DNA sequence of the nucleic acid fragments reported herein. More preferred nucleic acid fragments are at least 90% identical to the DNA sequence of the nucleic acid fragments reported herein. Most preferred are nucleic acid fragments that are at least 95% identical to the DNA sequence of the nucleic acid fragments reported herein.

A nucleic acid fragment is "hybridizable" to another nucleic acid fragment, such as a cDNA, genomic DNA, or RNA, when a single stranded form of the nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization. For preliminary screening for homologous nucleic acids, low stringency hybridization conditions, corresponding to a Tm of 55° C., can be used, e.g., 5×SSC, 0.1% SDS, 0.25% milk, and no formamide; or 30% formamide, 5×SSC, 0.5% SDS. Moderate stringency hybridization conditions correspond to a higher Tm, e.g., 40% formamide, with 5× or 6×SSC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridization decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridization with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. Preferably, a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

A "substantial portion" refers to an amino acid or nucleotide sequence which comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Basic Local Alignment Search Tool; Altschul et al., *J. Mol. Biol.* 215:403410 (1993)). In general, a sequence of ten or more contiguous amino acids or thirty or more nucleotides is needed in order to putatively identify a polypeptide or nucleic acid sequence as homologous to a known protein or gene. Moreover, with respect to nucleotide sequences, gene-specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of about 12-15 bases may be used as amplification primers in PCR (polymerase chain reaction) in order to obtain a particular nucleic acid molecule comprising the primers. Accordingly, a "substantial portion" of a nucleotide sequence comprises enough of the sequence to afford specific identification and/or isolation of a nucleic acid molecule comprising the sequence. The instant specification teaches partial or complete amino acid and nucleotide sequences encoding one or more particular proteins. The skilled artisan, having the benefit of the sequences as reported herein, may now use all or a substantial portion of the disclosed sequences for the purpose known to those skilled in the art. Accordingly, the instant invention may make use of the complete sequences as reported in the specification, as well as substantial portions of those sequences and substantially similar sequences as defined above.

The term "complementary" describes the relationship between nucleotide bases that are capable of hybridizing to one another. For example, with respect to DNA, adenosine is complementary to thymine and cytosine is complementary to guanine. Accordingly, the instant invention may make use of isolated nucleic acid molecules that are complementary to the complete sequences as reported in the accompanying Sequence Listing and the specification as well as those substantially similar nucleic acid sequences.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology*; Lesk, A. M., Ed.; Oxford University Press: New York, 1988; *Biocomputing: Informatics and Genome Projects*; Smith, D. W., Ed.; Academic Press: New York, 1993; *Computer Analysis of Sequence Data, Part I*; Griffin, A. M. and Griffin, H. G., Eds.; Humana Press: New Jersey, 1994; *Sequence Analysis in Molecular Biology*; von Heinje, G., Ed.; Academic Press: New York, 1987; and *Sequence Analysis Primer*; Gribskov, M. and Devereux, J., Eds.; Stockton Press: New York, 1991. Preferred methods to determine identity are designed to give the largest match between the sequences tested.

Methods to determine identity and similarity are codified in publicly available computer programs. Preferred computer program methods to determine identity and similarity between two sequences include, but are not limited to, the GCG Pileup program found in the GCG program package, using the Needleman and Wunsch algorithm with their standard default values of gap creation penalty=12 and gap extension penalty=4 (Devereux et al., *Nucleic Acids Res.* 12:387-395 (1984)), BLASTP, BLASTN, and FASTA (Pearson et al., *Proc. Natl. Acad. Sci. USA* 85:2444-2448 (1988)). The BLASTX program is publicly available from NCBI and other sources (*BLAST Manual*, Altschul et al., Natl. Cent. Biotechnol. Inf., Natl. Library Med. (NCBI NLM) NIH, Bethesda, Md. 20894; Altschul et al., *J. Mol. Biol.* 215:403-410 (1990); Altschul et al., "Gapped BLAST and PSI-BLAST: a new generation of protein database search programs", *Nucleic Acids Res.* 25:3389-3402 (1997)). Another preferred method to determine percent identity is by the method of DNASTAR protein alignment protocol using the Jotun-Hein algorithm (Hein et al., *Methods Enzymol.* 183:626-645 (1990)). Default parameters for the Jotun-Hein method for alignments are: for multiple alignments, gap penalty=11, gap length penalty=3; for pairwise alignments ktuple=6. As an illustration, by a polynucleotide having a nucleotide sequence having at least, for example, 95% "identity" to a reference nucleotide sequence it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having an amino acid sequence having at least, for example, 95% identity to a reference amino acid sequence is intended that the amino acid sequence of the polypeptide is identical to the reference sequence except that the polypeptide sequence may include up to five amino acid alterations per each 100 amino acids of the reference amino acid. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

The term "homologous" refers to a protein or polypeptide native or naturally occurring in a given host cell. The invention may include microorganisms producing homologous proteins via recombinant DNA technology.

The term "percent homology" refers to the extent of amino acid sequence identity between polypeptides. When a first amino acid sequence is identical to a second amino acid sequence, then the first and second amino acid sequences exhibit 100% homology. The homology between any two polypeptides is a direct function of the total number of matching amino acids at a given position in either sequence, e.g., if half of the total number of amino acids in either of the two sequences are the same then the two sequences are said to exhibit 50% homology.

"Codon degeneracy" refers to divergence in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "expression" refers to the transcription and translation to gene product from a gene coding for the sequence of the gene product.

The terms "plasmid" and "vector" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a regulatory DNA sequence and/or a coding sequence into a cell. "Transformation vector" refers to a specific vector containing a foreign gene or DNA sequence and having additional elements that facilitate transformation of a particular host cell. "Expression cassette" refers to a gene having elements in addition to a coding region that allow for enhanced expression of that gene in a foreign host.

Host Microorganisms

Suitable host microorganisms for the utilization of fructose as a carbohydrate source for production of glycerol and glycerol derivatives may be either prokaryotic or eukaryotic and are limited only by the host microorganism's ability to naturally transport fructose or to express a protein which enables fructose transport, a protein with fructokinase activity, and active enzymes for the glycerol pathway. Suitable host cells are microorganisms such as *Escherichia, Streptococcus, Agrobacterium, Bacillus, Corynebacterium, Lactobacillus, Clostridium, Gluconobacter, Saccharomyces, Kluyveromyces, Aspergillus, Pichia, Rhizopus, Citrobacter, Enterobacter, Klebsiella, Aerobacter, Schizosaccharomyces, Zygosaccharomyces, Candida, Hansenula, Debaryomyces, Mucor, Torulopsis, Methylobacter, Salmonella, Streptomyces*, and *Pseudomonas*. Preferred in the present invention are *Escherichia coli, Escherichia blattae, Klebsiella, Citrobacter*, and *Aerobacter*. These microorganisms are PTS$^-$ in their native state, or may be rendered PTS$^-$ through inactivation of a PTS gene as described below.

Disruption of Phosphoenolpyruvate-Glucose Phosphotransferase System

In production microorganisms, it is generally desirable to unlink the transport of sugars and the use of phosphoenolpyruvate (PEP) for phosphorylation of the sugars being transported, thereby conserving a molecule of ATP. Disruption of the PTS is accomplished, for example, by preventing expression of active PEP-glucose phosphotransferase system protein(s). The PTS may be inactivated (PTS$^-$) by disrupting expression of one or more of the endogenous genes encoding the proteins required in this type of transport. For example, genes encoding phosphocarrier protein (ptsH), phosphoenolpyruvate-protein phosphotransferase (ptsI), and glucose-specific IIA component (crr) may be disrupted singly or in any combination. Disruption may be by any of methods known to one skilled in the art such as, for example, by inserting DNA fragments into the promoter or coding region of the gene to block transcription or prevent translation of an active protein, or deleting the entire coding region. An alternative means of disruption is to make use of naturally occurring or induced mutations which prevent expression of active protein from one or more of the PTS genes. In addition, antisense or cosuppression methods may be used for gene inactivation.

Sugar Transport in PTS$^-$ Hosts

When the PTS is disrupted, an alternative sugar transport mechanism is needed for nutrient uptake. Microorganisms naturally take up sugars in a less efficient manner when PTS is not active. Transport methods may include by proton- or cation-linked permeases, and by ATP-binding cassette (ABC)-type carriers. Protein-mediated facilitated diffusion, an additional transport method, is desired since cellular metabolic energy is not required. Proteins are known which transport a variety of sugars in microorganisms. Protein facilitators for sugar transport have been identified in microorganisms, such as the galactose-proton symporter (GalP) of *Escherichia coli* and the arabinose-proton symporter of *Salmonella typhimurium*. These proteins transport multiple sugars such as glucose, fructose, galactose, and/or xylose. Proteins that are substantially similar to a GalP, or other sugar transport proteins which are able to transport fructose, such as those listed in Table 1, may be used for fructose transport in a PTS⁻ host. A GalP is the preferred transporter of fructose in the method of the present invention. *E. coli* GalP is most preferred.

type of fructose transport protein. Alternatively, the endogenous promoter of the galP gene may be replaced with a more highly active promoter. Also, an endogenous promoter may be altered in vivo by mutation, deletion, and/or substitution to increase its activity. In addition, the ribosome binding site in a prokaryotic gene may be mutated to improve expression.

The skilled person will appreciate that genes encoding fructose transport proteins isolated from various sources may be used in the present invention, as well as that amino acid

TABLE 1

Proteins for fructose transport, with homology to *E. coli* GalP provided.

| Organism | Accession Number | Gene Function | Amino Acid Sequence Similarity (%) |
|---|---|---|---|
| *Shigella flexneri* | gi[564802] NP708708.2 | Galactose-Proton Symporter | 97 |
| *Salmonella enterica* | gi[56415029] YP152104.1 | Galactose-Proton Symporter | 96 |
| *Salmonella typhimurium* | gi[16766318] NP461933.1 | Arabinose-Proton Symporter | 77 |
| *Escherichia coli* | gi[26249273] NP755313.1 | Arabinose-Proton Symporter | 77 |
| *Gluconobacter oxydans* | gi[58039274] YP191238.1 | Galactose-Proton Symporter | 74 |
| *Gluconobacter oxydans* | gi[58039118] YP191082.1 | Sugar-Proton Symporter | 73 |
| *Francisella tularensis* | gi[567085] YP170410.1 | Galactose-Proton Symporter | 64 |
| *Coxiella burnetii* | gi[29652696] NP819388.1 | Xylose-Proton Symporter | 62 |
| *Bacillus licheniformis* | gi[527875] YP093341.1 | Galactose-Proton Symporter | 60 |
| *Zymomonas mobilis* | gi[36551262] YP162101.1 | Glucose-Proton Symporter | 50 |

Fructose Transport Protein Activity Expression

Expression of a natural endogenous fructose transporting protein, such as from the *E. coli* galP gene, may provide fructose uptake for fructose utilization by the cells. The endogenous level of fructose uptake is generally not high enough for optimal fructose utilization. Increased expression of a protein with fructose transport capability is desirable for efficient use of fructose in the present invention. Expression of, for example, GalP may be increased using one of many methods known to one skilled in the art. For example, increased gene copy number may be provided by introducing a galP gene on a multicopy plasmid, or integrating one or more copies of a galP gene into the host genome. The introduced galP coding region(s) that are either on a plasmid or in the genome may be expressed from a highly active promoter. An integrated coding region may either be introduced as a part of a chimeric gene having its own promoter, or it may be integrated adjacent to a highly active promoter that is endogenous to the genome or in a highly expressed operon. The introduced fructose transport protein coding region(s) may either have the same DNA sequence as an endogenous galP coding region, or may be heterologous with a differing sequence encoding a GalP protein or a GalP homologous protein such as those listed in Table 1, or may be for another substitutions, deletions or additions that produce a substantially similar protein may be included in the encoded protein.

Fructose Utilization in Production of Microbial Products

Utilization of fructose as a carbon substrate in the production of microbial products requires the phosphorylation of fructose by an enzyme with fructokinase activity, thereby providing fructose-phosphate for further metabolism. Proteins named fructokinases (designated EC 2.7.1.4) and various hexose kinases having fructose phosphorylating activity (EC 2.7.1.3 and EC 2.7.1.1) may be expressed in host strains thereby providing fructose phosphorylating activity. Fructose phosphorylating activity may be exhibited by hexokinases and ketohexokinases. Representative genes encoding enzymes, from a variety of microorganisms, which may be used to produce increased fructokinase activity in a microbial production host strain are listed in Table 2. In addition, enzymes with fructose phosphorylating activity from other organisms are listed in Table 2. One skilled in the art will know that proteins that are substantially similar to a protein which is able to phosphorylate fructose (such as encoded by the genes listed in Table 2) may be used in the instant invention.

TABLE 2

Genes encoding enzymes with fructokinase activity, and corresponding EC numbers.

| Source | Accession number | Gene Name | EC Number |
|---|---|---|---|
| *Agrobacterium tumefaciens* | AE007977 AE007869 | scrK (fructokinase) | 2.7.1.4 |
| *Streptococcus mutans* | D13175 | scrK (fructokinase) | 2.7.1.4 |
| *Escherichia coli* | X81461 AF473544 | cscK (fructokinase) | 2.7.1.4 |
| *Enterococcus faecalis* | AE016950 AE016830 | cscK (fructokinase) | 2.7.1.4 |
| *Xanthomonas oryzae* pv. *oryzae* | AE013598 | scrK (fructokinase) | 2.7.1.4 |
| *Oryza sativa* | AB110164 | frk (fructokinase) | 2.7.1.4 |
| *Zea mays* | AY197773 | frk2 (fructokinase) | 2.7.1.4 |
| *Zea mays* | AY197772 | frk1 (fructokinase) | 2.7.1.4 |
| *Lycopersicon hirsutum* | AY325501 | frk2 (fructokinase) | 2.7.1.4 |
| *Lycopersicon esculentum* | U64817 | frk1 (fructokinase) | 2.7.1.4 |

TABLE 2-continued

Genes encoding enzymes with fructokinase activity, and corresponding EC numbers.

| Source | Accession number | Gene Name | EC Number |
| --- | --- | --- | --- |
| Homo sapiens (human) | BC006233 | KHK (ketohexokinase) | 2.7.1.3 |
| Bos taurus | BT020734 | KHK (ketohexokinase) | 2.7.1.3 |
| Saccharomyces cerevisiae | NC_001138 | HXK1, HKA (hexokinase) | 2.7.1.1 |
| Saccharomyces cerevisiae | NC_001139 | HXK2, SCI2, HKB (hexokinase) | 2.7.1.1 |
| Homo sapiens | NM_033500 | HK1 (hexokinase) | 2.7.1.1 |
| Homo sapiens | NM_000189 | HK2 (hexokinase) | 2.7.1.1 |

Endogenous fructokinases are generally expressed only at low levels, even under inducing conditions such as in the presence of sucrose or fructose. Fructokinase genes are not known to be widespread among native E. coli strains and the presence of a fructokinse gene does not always guarantee functional activity. Two identified genes encoding proteins with fructokinase activity, present in a relatively small number of E. coli strains, are not induced by fructose. The genes enable strains to grow on sucrose and are only induced in the presence of that disaccharide (Kornberg, H., 2002. Adv. Enz. Reg. 42:349-360). Fructose may also be phosphorylated through the activity of a kinase that is normally active on mannose, 2-deoxyglucose and glucosamine. However, this enzyme is rarely present above trace levels in E. coli, even when the cells are growing (marginally) on fructose (Kornberg, H., 2002. Adv. Enz. Reg. 42:349-360). Manipulation of the expression of an endogenous sucrose utilization operon, a mannokinase gene, or other gene encoding a protein able to phosphorylate fructose may be used to enhance fructokinase activity.

In the present invention, fructokinase activity is increased when it is higher than the activity found naturally in the host microorganism. An assay of fructokinase units per milligram of protein (U/mg) in the supernatant fraction of a disrupted microorganism cell preparation can be used to determine natural and increased fructokinase activity levels. For example, in an E. coli strain which has a natural level of fructokiinase activity of 0.62 U/mg, a level that is greater than 0.62 U/mg is an increased level. The increased fructokinase activity may be well above 0.62 U/mg, such as at 9 U/mg or higher. A fructokinase activity level of over 22 U/mg is also increased activity.

Increased levels of fructokinase activity may be achieved by methods known to one skilled in the art as described above for GalP expression. These methods include means of increasing expression from an endogenous gene, as well as methods of introdoucing a gene to obtain increased expression.

Either an endogenous fructokinase coding region sequence or an exogenous one, such as one listed in Table 2, may be used for high expression of fructokinase activity in a host. A fructokinase coding region sequence may be isolated using PCR (see, e.g., U.S. Pat. No. 4,683,202) and primers designed to bound the desired sequence, if this sequence is known. This method was used in the examples in the isolation of the fructokinase coding regions of Streptococcus mutans and Agrobacterium tumefaciens. Other methods of gene isolation are well known to one skilled in the art such as by using degenerate primers or heterologous probe hybridization.

The skilled person will appreciate that genes encoding proteins with fructokinase activity isolated from other sources may be used in the present invention, as well as that amino acid substitutions, deletions or additions that produce a substantially similar protein may be included in the encoded protein.

Enhancement of Fructose Utilization with Deletion of yqhE

Deletion of the yqhE coding region may be employed to increase the ability of a host microorganism to utilize fructose in the production of microbial products. The yqhE gene encodes a protein that catalyzes the NAD(P)H dependent reduction of keto-esters. A typical keto-reductase is encoded by the yqhE gene of E. coli (GenBank®, Accession # U00096). The yqhE disruption-related enhanced production may be obtained through any method of disrupting the expression of the yqhE gene. In addition to deleting the entire yqhE coding region, inactivation of this gene may be accomplished, for example, by deleting a portion of the coding region, deleting or mutating the promoter responsible for its expression, mutating the coding region so that the protein is not produced such as by inserting a stop codon, inserting a DNA fragment, or by other methods known to one skilled in the art. In addition, cosuppression or antisense methods may be used to disrupt expression of the coding region. Disruption of genes homologous to yqhE may be used to increase the ability of a host microorganism to utilize fructose in the production of microbial products.

Glycerol Production in Microorganisms

Biological processes for the preparation of glycerol using carbohydrates or sugars are known in yeasts and in some bacteria, other fungi, and algae. Both bacteria and yeasts produce glycerol by converting glucose or other carbohydrates through the fructose-1,6-bisphosphate pathway in glycolysis or the Embden Meyerhof Parnas pathway. In the present invention, strains may be used that naturally produce glycerol. In addition, strains may be engineered for production of glycerol and glycerol derivatives for use in the present invention. The capacity for glycerol production from a variety of substrates may be provided through the expression of the enzyme activities glycerol-3-phosphate dehydrogenase (G3PDH) and/or glycerol-3-phosphatase as described in WO 99/28480 (E. I. du Pont de Nemours and Company ("DuPont")) which is herein incorporated by reference. Genes encoding these proteins that may be used for expressing the enzyme activities in a host microorganism are described in WO 99/28480.

Increased production of glycerol may be attained through reducing expression of target endogenous genes. Disruptions in endogenous genes encoding glycerol kinase and glycerol dehydrogenase activities further enhance glycerol production as described in WO 99/28480. Increased channeling of carbon to glycerol may be accomplished by reducing the expression of the endogenous gene encoding glyceraldehyde 3-phosphate dehydrogenase, as described in U.S. Published Patent Application No. 2004/0152174. Disruption may be by any method known to one skilled in the art, for example, as described above for the yqhE gene.

Glycerol provides a substrate for microbial production of useful products. Examples of these glycerol derivatives include 3-hydroxypropionic acid (3-HPA), methylglyoxal, 1,2-propanediol, and 1,3-propanediol.

Production of the Glycerol Derivative 1,3-propanediol

The glycerol derivative1,3-propanediol is a monomer having potential utility in the production of polyester fibers and the manufacture of polyurethanes and cyclic compounds. Bacterial strains have been engineered using combinations of alterations of genes to provide more efficient production of glycerol and the glycerol derivative 1,3-propanediol. For example, WO 96/35796 (U.S. Pat. No. 5,686,276, DuPont) discloses a method for the production of 1,3-propanediol starting with a carbon substrate other than glycerol or dihydroxyacetone (especially, e.g., glucose), using a single microorganism comprising a dehydratase activity. WO 99/28480 (DuPont) discloses a similar method with advantages derived from expressing exogenous activities of one or both of glycerol-3-phosphate dehydrogenase and glycerol-3-phosphate phosphatase while disrupting one or both of endogenous activities glycerol kinase and glycerol dehydrogenase. WO 98/21339 (U.S. Pat. No. 6,013,494, DuPont) describes a process for the production of 1,3-propanediol using a single microorganism comprising exogenous glycerol-3-phosphate dehydrogenase, glycerol-3-phosphate phosphatase, dehydratase, and 1,3-propanediol oxidoreductase (e.g., dhaT). WO 98/21341 (U.S. Pat. No. 6,136,576, DuPont) discloses a method for the production of 1,3-propanediol comprising a recombinant microorganism further comprising a dehydratase and protein X (later identified as being a dehydratase reactivation factor peptide). WO 2001/012833 (DuPont) describes an improvement to the process where a significant increase in titer (grams product per liter) is obtained by virtue of a non-specific catalytic activity (distinguished from 1,3-propanediol oxidoreductase encoded by dhaT) to convert 3-hydroxypropionaldehyde to 1,3-propanediol. U.S. patent application Ser. No. 10/420587 (2003) (U.S. Provisional Application Ser. No. 60/374931 (2002), DuPont)) discloses vectors and plasmids useful for the production of 1,3-propanediol. The DuPont applications are incorporated by reference in the instant specification as though set forth in their entirety herein.

Increased production of 1,3-propanediol may be achieved by further modifications to a host strain, including reduced expression of some target genes and increased expression of other target genes, described in co-owned and copending application U.S. Published Patent Application No. 2004/0152174. For utilization of glucose as a carbon source in a PTS$^-$ host, expression of glucokinase activity may be increased. Use of mixed carbon sources containing glucose and fructose may be increased in efficiency in a strain with increased expression of both glucokinase and fructokinase.

Additional genes whose increased or up-regulated expression increases 1,3-propanediol production include genes encoding:

phosphoenolpyruvate carboxylase typically characterized as EC 4.1.1.31 cob(I)alamin adenosyltransferase, typically characterized as EC 2.5.1.17 non-specific catalytic activity that is sufficient to catalyze the interconversion of 3-HPA and 1,3-propanediol, and specifically excludes 1,3-propanediol oxidoreductase (s), typically these enzymes are alcohol dehydrogenases Genes whose reduced or down-regulated expression increases 1,3-propanediol production include genes encoding:
aerobic respiration control protein
methylglyoxal synthase
acetate kinase
phosphotransacetylase
aldehyde dehydrogenase A
aldehyde dehydrogenase B
triosephosphate isomerase
phosphogluconate dehydratase Gene Expression Manipulation Up-regulation or down-regulation may be achieved by a variety of methods which are known to those skilled in the art. It is well understood that up-regulation or down-regulation of a gene refers to an alteration in the level of activity present in a cell that is derived from the protein encoded by that gene relative to a control level of activity, for example, by the activity of the protein encoded by the corresponding (or non-altered) wild-type gene.

Specific genes involved in an enzyme pathway may be up-regulated to increase the activity of their encoded function (s). For example, additional copies of selected genes may be introduced into the host cell on multicopy plasmids such as pBR322. Such genes may also be integrated into the chromosome with appropriate regulatory sequences that result in increased activity of their encoded functions. The target genes may be modified so as to be under the control of non-native promoters or altered native promoters. Endogenous promoters can be altered in vivo by mutation, deletion, and/or substitution.

Alternatively, it may be useful to reduce or eliminate the expression of certain genes relative to a given activity level. Methods of down-regulating and disrupting genes are known to those of skill in the art. Down-regulation can occur by deletion, insertion, or alteration of coding regions and/or regulatory (promoter) regions. Specific down regulations may be obtained by random mutation followed by screening or selection, or, where the gene sequence is known, by direct intervention by molecular biology methods known to those skilled in the art. A particularly useful, but not exclusive, method to effect down-regulation is to alter promoter strength.

Disruptions of genes may be used to either prevent expression of the protein of interest or result in the expression of a protein that is non-functional. This may be accomplished for example, by 1) deleting coding regions and/or regulatory (promoter) regions, 2) inserting exogenous nucleic acid sequences into coding regions and/regulatory (promoter) regions, and 3) altering coding regions and/or regulatory (promoter) regions (for example, by making DNA base pair changes). Specific disruptions may be obtained by random mutation followed by screening or selection, or, in cases where the gene sequences in known, specific disruptions may be obtained by direct intervention using molecular biology methods know to those skilled in the art. A particularly useful method is the deletion of significant amounts of coding regions and/or regulatory (promoter) regions.

Methods of altering recombinant protein expression are known to those skilled in the art, and are discussed in part in Baneyx, *Curr. Opin. Biotechnol.* (1999) 10:411; Ross, et al., *J Bacteriol.* (1998) 180:5375; deHaseth, et al., *J. Bacteriol.* (1998) 180:3019; Smolke and Keasling, *Biotechnol. Bioeng.* (2002) 80:762; Swartz, *Curr. Opin. Biotech.* (2001) 12:195; and Ma, et al., *J. Bacteriol.* (2002) 184:5733.

Construction of Recombinant Organisms

Recombinant organisms containing the necessary changes in gene expression for utilizing fructose in the production of microbial products including glycerol and glycerol derivatives, may be constructed using techniques well known in the art, some of which are exemplified in the Examples herein.

Vectors and Expression Cassettes

The construction of recombinant microorganisms of the present invention may be accomplished using a variety of vectors and transformation and expression cassettes suitable for the cloning, transformation and expression of coding regions that confer the ability to utilize fructose in the production of glycerol and its derivatives in a suitable host cell. Suitable vectors are those which are compatible with the microorganism employed. Suitable vectors can be derived, for example, from a bacterium, a virus (such as bacteriophage T7 or a M-13 derived phage), a cosmid, a yeast or a plant. Protocols for obtaining and using such vectors are known to those skilled in the art (Sambrook et al., supra).

Initiation control regions, or promoters, which are useful to drive expression of coding regions for the instant invention in the desired host cell are numerous and familiar to those skilled in the art. Virtually any promoter capable of driving expression is suitable for the present invention including but not limited to CYC1, HIS3, GAL1, GAL10, ADH1, PGK, PHO5, GAPDH, ADC1, TRP1, URA3, LEU2, ENO, and TPI (useful for expression in *Saccharomyces*); AOX1 (useful for expression in *Pichia*); and lac, trp, $\lambda P_L$, $\lambda P_R$, T7, tac, and trc (useful for expression in *E. coli*).

Termination control regions may also be derived from various genes native to the preferred hosts. Optionally, a termination site may be unnecessary; however, it is most preferred if included.

For effective expression of the instant enzymes, DNA sequences encoding the enzymes are linked operably through initiation codons to selected expression control regions such that expression results in the formation of the appropriate messenger RNA. Co-owned and copending application U.S. Published Patent Application No. 2004/0152174 describes vectors that were used in construction of 1,3-propanediol producing strains. Vector pSYCO109 is used herein for the construction of fructose utilizing strains. The essential elements of pSYCO109 are derived from the dha regulon isolated from *Klebsiella pneumoniae* and from *Saccharomyces cerevisiae*. It contains the open reading frames dhaB1, dhaB2, dhaB3, dhaX, orfX, DAR1, and GPP2 arranged in three separate operons, the nucleotide sequence of which is included in SEQ ID NO:1. The promoter ("p-") and the open reading frames contained within each "( )" represent the composition of an operon:

pSYCO109 (SEQ ID NO:1):
  p-trc (Dar1_GPP2) same orientation compared to the other 2 pathway operons,
  p-1.6 long GI (dhaB1_dhaB2_dhaB3_dhaX), and
  p-1.6 long GI (orfY_orfX).

Transformation of Suitable Hosts and Expression of Genes for Utilization of Fructose in Production of Microbial Products Once suitable cassettes are constructed, they are used to transform appropriate host cells. Introduction of the cassette containing coding regions of, for example, fructokinase and galP into the host cell may be accomplished by known procedures such as by transformation (e.g., using calcium-permeabilized cells, or electroporation) or by transfection using a recombinant phage virus (Sambrook et al., supra). Expression cassettes may be maintained on a stable plasmid in a host cell. In addition, expression cassettes may be integrated into the genome of the host cell through homologous or random recombination using vectors and methods well known to those skilled in the art. Site-specific recombination systems may also be used for genomic integration of expression cassettes.

Mutants

In addition to the cells exemplified, the present method may make use of cells having single or multiple mutations specifically designed to enhance the production of microbial products including glycerol and/or its derivatives. Cells that normally divert a carbon feed stock into non-productive pathways, or that exhibit significant catabolite repression may be mutated to avoid these phenotypic deficiencies.

Methods of creating mutants are common and well known in the art. A summary of some methods is presented in U.S. Published Patent Application No. 2004/0152174. Specific methods for creating mutants using radiation or chemical agents are well documented in the art. See, for example, Thomas D. Brock in Biotechnology: *A Textbook of Industrial Microbiology*, Second Edition (1989) Sinauer Associates, Inc., Sunderland, Mass., or Deshpande, Mukund V., *Appl. Biochem. Biotechnol.* 36, 227 (1992).

After mutagenesis has occurred, mutants having the desired phenotype may be selected by a variety of methods. Random screening is most common where the mutagenized cells are selected for the ability to produce the desired product or intermediate. Alternatively, selective isolation of mutants can be performed by growing a mutagenized population on selective media where only resistant colonies can develop. Methods of mutant selection are highly developed and well known in the art of industrial microbiology. See, for example, Brock, Supra; DeMancilha et al., *Food Chem.* 14, 313 (1984).

Media and Carbon Substrates

Fermentation media in the present invention contain fructose as a carbon substrate. Fructose may be one of multiple carbon substrates in the media, including for example glucose, lactose, and/or sucrose.

In addition to the carbon substrate, fermentation media contains, for example, suitable minerals, salts, cofactors, buffers and other components, known to those skilled in the art, suitable for the growth of the cultures and promotion of the enzymatic pathway necessary for production of glycerol and its derivatives, for example 1,3-propanediol. Particular attention is given to Co(II) salts and/or vitamin $B_{12}$ or precursors thereof in production of 1,3-propanediol since adenosylcobalamin (coenzyme $B_{12}$) is an essential cofactor for dehydratase activity, as described in U.S. Published Patent Application No. 2004/0152174.

Culture Conditions:

Typically cells are grown at 35° C. in appropriate media containing fructose. Preferred growth media in the present invention are common commercially prepared media such as Luria Bertani (LB) broth, Sabouraud Dextrose (SD) broth or Yeast medium (YM) broth. Other defined or synthetic growth media may also be used, and the appropriate medium for growth of the particular microorganism will be known by someone skilled in the art of microbiology or fermentation science. The use of agents known to modulate catabolite repression directly or indirectly, e.g., cyclic adenosine 2':3'-monophosphate, may also be incorporated into the reaction media. Similarly, the use of agents known to modulate enzymatic activities (e.g., methyl viologen) that lead to enhancement of 1,3-propanediol production may be used in conjunction with or as an alternative to genetic manipulations with 1,3-propanediol production strains.

Suitable pH ranges for the fermentation are between pH 5.0 to pH 9.0, where pH 6.0 to pH 8.0 is preferred as the initial condition.

Reactions may be performed under aerobic or anaerobic conditions where aerobic, anoxic, or anaerobic conditions are preferred based on the requirements of the microorganism. Fed-batch fermentations may be performed with carbon feed, for example, fructose, limited or excess.

Batch and Continuous Fermentations:

Batch fermentation is a commonly used method. Classical batch fermentation is a closed system where the composition of the media is set at the beginning of the fermentation and is not subject to artificial alterations during the fermentation. Thus, at the beginning of the fermentation, the media is inoculated with the desired microorganism or microorganisms and fermentation is permitted to occur adding nothing to the system. Typically, however, "batch" fermentation is batch with respect to the addition of carbon source, and attempts are often made at controlling factors such as pH and oxygen concentration. In batch systems, the metabolite and biomass compositions of the system change constantly up to the time the fermentation is stopped. Within batch cultures, cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the Fed-Batch system. Fed-Batch fermentation processes are also suitable in the present invention and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch fermentations are common and well known in the art and examples may be found in Brock, supra.

Continuous fermentation is an open system where a defined fermentation media is added continuously to a bioreactor and an equal amount of conditioned media is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems, a number of factors affecting growth can be altered continuously while the cell concentration, measured by media turbidity, is kept constant.

Continuous systems strive to maintain steady state growth conditions, and thus the cell loss due to media being drawn off must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

It is contemplated that the present invention may be practiced using batch, fed-batch or continuous processes and that any known mode of fermentation would be suitable. Additionally, it is contemplated that cells may be immobilized on a substrate as whole cell catalysts and subjected to fermentation conditions for production of glycerol and glycerol derivatives, including 1,3-propanediol.

General Methods and Materials

Procedures for phosphorylations, ligations and transformations are well known in the art. Techniques suitable for use in the following examples may be found in Sambrook, J. et al., supra.

Materials and methods suitable for the maintenance. and growth of bacterial cultures are well known in the art. Techniques suitable for use in the following examples may be found in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994) or Thomas D. Brock in *Biotechnology: A Textbook of Industrial Microbiology*, Second Edition (1989) Sinauer Associates, Inc., Sunderland, Mass. All reagents and materials used for the growth and maintenance of bacterial cells were obtained from DIFCO Laboratories (Detroit, Mich.), GIBCO/BRL (Gaithersburg, Md.), or Sigma-Aldrich (St. Louis, Mo.) unless otherwise specified.

The production of glycerol and conversion of glycerol to 1,3-propanediol was monitored by HPLC. Analyses were performed using standard techniques and materials available to one of skill in the art of chromatography. One suitable method utilized a Waters Maxima 820 HPLC system using UV (210 nm) and RI detection. Samples were injected onto a Shodex SH-1011 column (8 mm×300 mm, purchased from Waters, Milford, Mass.) equipped with a Shodex SH-1011 P precolumn (6 mm×50 mm), temperature controlled at 50° C., using 0.01 N $H_2SO_4$ as mobile phase at a flow rate of 0.5 ml/min. When quantitative analysis was desired, samples were prepared with a known amount of trimethylacetic acid as external standard. Typically, the retention times of glucose (RI detection), glycerol, 1,3-propanediol (RI detection), and trimethylacetic acid (UV and RI detection) were 15.27 min, 20.67 min, 26.08 min, and 35.03 min, respectively.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

The meaning of abbreviations is as follows: "hr" means hour(s), "min" means minute(s), "sec" means second(s), "d" means day(s), "µl" means microliter(s), "ml" means milliliters, "L" means liters, "µM" means micromolar "mM" means millimolar, "nm" means nanometer, "g" means gram(s), "ng" means nanogram(s), and "kg" means kilogram(s), "HPLC" means high performance liquid chromatography, "RI" means refractive index, "bp" means base pairs, "U/ml" means units per ml, and "PDO" means 1,3-propanediol.

Example 1

Isolation of the scrK Fructokinase Encoding Gene from *Streptococcus Mutans* by PCR Genomic DNA was prepared from *Streptococcus mutans* (ATCC 25175D) using the protocol described in Jagusztyn et al. (J. Gen. Microbiol. 128:1135-1145(1982)). PCR primers (SEQ ID NO:2 and SEQ ID NO:3) were designed based on the *Streptococcus mutans* (scrK) DNA sequence (Sato et. al., J. Gen. Microbiol. 139 (5), 921-927 (1993)) for amplifying the scrK coding region. The nucleotide sequences corresponding to Sacl and Pacl restriction enzyme sites were also incorporated into the 5' and 3' PCR primers, respectively. The *Streptococcus mutans* scrK coding region was amplified using the standard PCR protocol included with the HotStart-Taq™ kit (Qiagen, Valencia, Calif.). The PCR reaction contained 1 ng of genomic DNA and was 1 µM for each primer. The resulting 883 bp DNA fragment was digested with the enzymes Sacl and Pacl. The digested fragment was cloned directly into the plasmid pSYCO109 (spec$^R$; SEQ ID NO:1; described in U.S. patent application Ser. No. 10/420,587) which was also digested with the same two restriction enzymes. In the resulting plasmid, upstream (5') of the scrK coding region fragment is a lexA terminator, followed by a GI (glucose isomerase gene from *Streptomyces lividans*) promoter. Downstream (3') of the scrK coding region fragment is the rrnBT1T2 terminator from pTrc99A (Amersham Pharmacia Biotech, Piscataway, N.J.).

The plasmid, designated pSCRK, containing the complete scrK coding sequence, was transformed into *E. coli* DH5α cells using the manufacturer's protocol (Invitrogen, Carlsbad, Calif.). The cells were plated on Luria Broth (LB) medium (BD, Sparks, Md.) containing 100 µg/ml spectinomycin and incubated overnight at 37° C.

Fructokinase Assay

Individual transformed colonies, containing the plasmid pSCRK, were selected and tested for fructokinase activity. Cells were grown in 10 ml of LB media for 24 hrs. at 35° C., harvested by centrifugation and suspended in buffered solution containing 10 mM Tris-HCl (pH 7.5). Cells were disrupted by sonication and cell debris was removed by centrifugation. The supernatant was assayed for total protein concentration using the Bradford assay (Bradford, M. M., Anal. Biochem. 72:248-254 (1976)).

Fructokinase activity was determined by an enzyme linked assay. The assay buffer contained 5 mM Tris-HCl buffer, pH 8.5 with 13.3 mM MgCl$_2$, 0.67 M fructose, 16.5 mM ATP, 6.8 mM NAD, 300 U/ml G-6-P dehydrogenase, 300 U/ml Phosphoglucoisomerase (PGI), and 20-50 µl of total protein extract. Assays measuring the conversion of NAD to NADH were run for 10 minutes at 30° C. and monitored at 340 nm. In this assay, fructose is converted to F-6-P by fructokinase, F-6-P is isomerized to G-6-P by PGI, and G-6-P is converted to 6-P-G by dehydrogenase, using NAD. NAD conversion to NADH is easily detected at 340 nm.

Greatly enhanced fructokinase activity was demonstrated in extracts from cells containing the pSCRK plasmid. Low activity was found in negative control lines (cells containing the plasmid pSYCO109). Specific activity obtained for each cell line tested is listed in Table 3.

TABLE 3

E. coli Containing the S. mutans scrK Gene: Fructokinase specific activity

| Name | Specific Activity (U/mg) |
|---|---|
| DH5α (neg. control) | 0.62 |
| DH5α (pSCRK-1) | 9.33 |
| DH5α (pSCRK-2) | 11.24 |
| DH5α (pSCRK-3) | 10.55 |

Example 2

Fructose Utilization in PTS$^-$ Host with Enhanced Fructokinase and GalP Expression Individual colonies that demonstrated fructokinase activity were used as a source of plasmid DNA to be transformed into the *E. coli* strain Triple Triple ΔaldA ΔaldB (TTab; described in U.S. Patent Application No. 2004/0152174). TTab is a PTS$^-$ strain resulting from a deletion in the ptsHlcrr operon. In the TTab strain, a galP coding region is expressed from a trc promoter, providing constitutive, high level expression of GalP activity.

One microgram of plasmid DNA prepared from each of DH5α pSCRK-1 and DH5α pSCRK-2 cells was used to transform TTab cells, and transformants were selected by plating on LB media containing 100 µg/ml spectinomycin. Confirmation that transformed cells contained the expected plasmid was performed by isolating plasmid DNA using a Qiagen (Valencia, Calif.) QIAprep™ miniprep kit, digesting the plasmid with the enzymes Sacl and Pacl, and comparing the resulting digestion fragments to the original plasmid control (from DH5α cells described above) on agarose gels. Cells that contained intact plasmid with the scrK gene were further tested for fructose utilization by shake-flask assays.

Single colonies from each of two clones called TTab pSCRK-1 and TTab pSCRK-2, derived from DH5α pSCRK-1 and DH5α pSCRK-2, respectively, were used to inoculate 25.0 mL of TM3 medium (potassium phosphate, 7.5 g/L; citric acid, 2.0 g/L; ammonium sulfate, 3.0 g/L; magnesium sulfate, 2.0 g/L; calcium chloride, 0.2 g/L; ferric ammonium citrate, 0.33 g/L; yeast extract (Difco-BD, Sparks, MD) 0.5 g/L; 10 ml/L trace elements (recipe below); adjust pH to 6.5. TM3 media was supplemented with fructose (10 g/L) as the sole carbohydrate source.
Trace Elements: (Use 10 ml/L)
Citric Acid*1 H$_2$O—190 µM
MgSO$_4$*H$_2$O—178 µM
NaCl—171 µM
FeSO$_4$*7 H$_2$O—4 µM
CoCl$_2$*6 H$_2$O—4 µM
ZnSO$_4$*7 H$_2$O—3 µM
CuSO$_4$*5 H$_2$O—0.4 µM
H$_3$BO$_4$—2 µM
NaMoO$_4$*2 H$_2$O—0.5 µM Cultures were grown for 24 hr at 35° C. Fructose utilization was established by determining cell mass accumulation through optical density (A600 nm) measurements. The results in Table 4 demonstrate greatly enhanced cell mass accumulation in cells containing the *S. mutans* scrK gene (compared to the negative control).

TABLE 4

Fructose Utilization in Cells Expressing the *S. mutans* scrK Gene

| Name | OD A600 |
|---|---|
| TTab (neg. control) | 0.23 |
| TTab (pSCRK-1) | 4.84 |
| TTab (pSCRK-2) | 4.88 |

Fructose consumption was determined by HPLC analysis (see General Methods). Following tests for cell mass accumulation by optical density, cells were removed by centrifugation and the supernatant used to determine fructose concentration. A low level of fructose consumption was shown for cells with no added fructokinase gene (negative control), while cells containing the *S. mutans* scrK gene showed greatly enhanced utilization of fructose (Table 5).

TABLE 5

Fructose Utilization in Cells Expressing the *S. mutans* scrK Gene

| Name | Fructose Utilization (%) |
|---|---|
| TTab (neg. control) | 4% |
| TTab (pSCRK-1) | 74% |
| TTab (pSCRK-2) | 79% |

Glycerol Accumulation Due to Expression of scrK Gene

The ability of an *E. coli* strain containing the *S. mutans* scrK gene to produce fermentation products using fructose as a substrate was characterized by culturing cells in shake flasks containing TM3 medium with fructose (10 g/L) as the sole carbohydrate source for 24 hr.

The GI promoter-*S. mutans* scrK gene was first transferred to an alternate plasmid, pSYCO400, resulting in Rho-independent transcription terminator sequences flanking the promoter-gene insertion. PSYCO400 was constructed from pSYCO109 (SEQ ID NO:1) by first adding a Hindlil-XbaI DNA fragment containing the mutated dhaB genes, 20-B9, described in WO 2004/056963. Next a synthesized DNA fragment containing a multiple cloning site (MCS; SEQ ID NO:4) was added between gpp2 and a spectinomycin resistance marker. The MCS, which contains restriction enzyme recognition sites for Asc I-Nhe I-Pac I-Rsr II-Nsi I-Sac I-Mlu I-Pme I-Age I-Sap I-SnaB I, was added to facilitate subsequent cloning steps. Following addition of the MCS, transcription termination sequences (LeuA and LexA, Miller, J. H. 1992, A Short Course in Bacterial Genetics. Cold Spring Harbor, N.Y.: Cold Spring Harbor Laboratory Press) were added by ligation of oligonuleotides to the plasmid. The LexA terminator (SEQ ID NO:5) was added at the 5'-end of the MCS (nearest the Asc I restriction enzyme site) and the LeuA terminator (SEQ ID NO:6) was added at the 3'-end (nearest the SnaB I site). The resulting plasmid was designated pSYCO400. The *S. mutans* scrK gene was ligated into pSYCO400 by digesting the plasmid pSCRK with the enzymes PmeI and SacI, isolating the fragment containing the gene and promoter, then ligating into pSYCO400 digested with the same restriction enzymes. The resulting plasmid was designated pSYCO400/SCRK.

Accumulation of cell mass (by OD600) and glycerol (by HPLC as described in General Methods) were determined and compared to the results from a negative control line (same plasmid with no fructokinase gene). The results in Table 6 demonstrate that greatly enhanced fructose conversion into product (cell mass and glycerol) was seen in the *E. coli* line containing the *S. mutans* scrK gene.

TABLE 6

Fermentation Products Accumulated in *E. Coli* Containing the scrK Gene

| Name | Glycerol (g/L) | OD600 |
|---|---|---|
| TTab pSYCO400 (negative control) | ND | 0.24 |
| TTab pSYCO400/SCRK-1 | 3.00 | 5.72 |
| TTab pSYCO400/SCRK-2 | 2.32 | 7.72 |

ND = not detected

Example 3

Isolation of a the scrK (Fructokinase Encoding) Gene from *Agrobacterium tumefaciens* by PCR Genomic DNA was prepared from *Agrobacterium tumefaciens* strain C58 using a Genomic-Tip™ DNA isolation kit (Qiagen, Valencia, Calif.). PCR primers (SEQ ID NO:7 and SEQ ID NO:8) were designed based on the *Agrobacterium tumefaciens* scrK coding region DNA sequence (Wood et al., Science 294 (5550), 2317-2323 (2001)). The nucleotide sequence corresponding to SacI and PacI restriction enzyme sites was also incorporated into the PCR primers. The scrK gene was amplified using the standard PCR protocol included with the HotStartTaq™ kit (Qiagen, Valencia, Calif.).

Reactions contained 1 ng of genomic DNA and 1 µM each of primers. The resulting 978 bp DNA fragment was digested with the enzymes SacI and PacI. The digested fragment was cloned directly into the plasmid pSYCO109 (spec$^R$; described in U.S. patent application Ser. No. 10/420,587) or into the plasmid pSYCO400 (described above) which had been digested with the same two restriction enzymes.

The plasmids, designated pAGRO and pSCYO400/AGRO respectively, containing the complete scrK coding sequence, were transformed into *E. coli* DH5α or TTab cells and plated on Luria Broth (LB) medium containing 100 µg/ml spectinomycin.

Fructokinase Assay

Individual transformed *E. coli* DH5α colonies, containing the plasmid pAGRO, were selected and tested for fructokinase activity as described above. Greatly enhanced fructokinase activity was demonstrated in protein extracts from cells containing the *Agrobacterium tumefaciens* scrK gene. No activity was detected in negative control lines (cells containing empty plasmid pSYCO109). Specific activity for each cell line is listed in Table 7.

TABLE 7

*E. coli* Containing the *A. tumefaciens* scrK Gene - Fructokinase specific activity

| Name | Specific Activity (U/mg) |
|---|---|
| DH5α (neg. control) | ND |
| DH5α (pAGRO-1) | 22.20 |
| DH5α (pAGRO-2) | 16.83 |

ND = not detected

Example 4

Fructose Utilization in PTS⁻ Host with the *A. tumefaciens* scrK Gene and Enhanced GalP Expression Glycerol Accumulation Due to Expression of scrK Gene Individual TTab colonies containing the plasmid pSYCO400/AGRO were selected and used to test for fermentation product accumulation using fructose as a substrate. Cells were grown in TM3 media, harvested and prepared as described above. Supernatants were analyzed for glycerol and 1,3-Propanediol (PDO) accumulation by HPLC (see General Methods). Accumulation of PDO was accomplished through the addition of Vitamin $B_{12}$ (0.1 mg/L) into TM3 media. The results in Table 8 demonstrate successful conversion of fructose into the products cell mass, glycerol and PDO. Product accumulation was greatly enhanced in TTab lines containing the *A. tumefaciens* scrK gene. The strains TTab pSYCO400/AGRO-1 and TTab pSYCO400/AGRO-2, represent two independently isolated colonies.

TABLE 8

Fermentation Products Accumulated in *E. Coli* Containing the scrK Gene

| Name | Glycerol (g/L) | PDO* (g/L) | OD600 |
|---|---|---|---|
| TTab pSYCO400 (negative control) | 0.01 | ND | 0.32 |
| TTab pSYCO400/AGRO-1 | 2.42 | 1.18 | 1.15 |
| TTab pSYCO400/AGRO-2 | 1.87 | 1.44 | 0.93 |

*1,3-Propanediol
ND = not detected

Utilization of Fructose in a Mixed Carbohydrate Source

Individual TTab colonies were selected and used to test for fermentation product accumulation using a mixed sugar feedstock. Cells were cultured in TM3 media containing fructose as the sole carbohydrate source, glucose as the sole carbohydrate or in media containing a mixture of equal amounts of fructose and glucose. Cells were grown, harvested and prepared as described in Example 1. Cell mass accumulation was determined by optical density (A600 nm) measurements. Culture supernatants were analyzed for glycerol and PDO accumulation by HPLC (see General Methods). The results in Table 9 demonstrated good cell mass accumulation in cells containing the *A. tumefaciens* scrK gene when grown in fructose, glucose and in media containing a fructose/glucose mixture. Negative control cells (with no fructokinase gene added) grew well in glucose and to a lesser extent in the fructose/glucose mixture, indicating much less efficient utilization of fructose in the absence of the added recombinant fructokinase gene.

TABLE 9

Cell Mass Accumulation (OD A600) in Mixed Carbohydrate Feed

| Source Carbohydrate | TTab pSYCO400/AGRO-1 (Fructokinase⁺) | TTab pSYCO400 (negative control) |
|---|---|---|
| Fructose | 1.15 | 0.16 |
| Glucose | 2.96 | 3.47 |
| Glucose + Fructose | 3.16 | 2.63 |

The results in Table 10 demonstrate that cells containing the *A. tumefaciens* scrK gene readily accumulate glycerol in media containing fructose as the sole carbohydrate. The data in Table 10 also shows glycerol accumulation in media containing a mixed feedstock of fructose and glucose, again demonstrating utilization of fructose as a substrate for production of fermentation products.

TABLE 10

Glycerol Accumulation (g/L) in Mixed Carbohydrate Feed

| Source Carbohydrate | TTab pSYCO400/AGRO-1 (Fructokinase⁺) g/L | TTab pSYCO400 (negative control) g/L |
|---|---|---|
| Fructose | 1.21 | 0.03 |
| Glucose | 3.56 | 3.12 |
| Glucose + Fructose | 3.33 | 2.03 |

The results in Table 11 show that cells containing the *A. tumefaciens* scrK gene readily accumulate PDO in media containing fructose as the sole carbohydrate, as compared to the negative control line (with no fructokinase gene). The data in Table 9 also shows PDO accumulation in media containing a mixture of fructose and glucose and, therefore, fructose conversion using a mixed sugar feedstock for production of fermentation products.

TABLE 11

PDO Accumulation (g/L) in Mixed Carbohydrate Feed

| Source Carbohydrate | TTab pSYCO400/AGRO-1 (Fructokinase⁺) g/L | TTab pSYCO400 (negative control) g/L |
|---|---|---|
| Fructose | 0.89 | 0.03 |
| Glucose | 1.21 | 1.25 |
| Glucose + Fructose | 1.80 | 1.09 |

Example 5

Fructose Utilization in PTS⁻ *E. coli* Without Enhanced GalP

Individual colonies containing the pSYCO/AGRO plasmid that demonstrated fructokinase activity above, were used as a source of plasmid DNA to be transformed into the *E. coli* PTS⁻ strain KLndh81 (described in U.S. Patent Application No. 2004/0152174). Confirmation that transformed cells contained the fructokinase expression cassette was performed by plasmid isolation and analysis methods described above.

Single colonies containing the fructokinase gene in the PTS⁻ TTab and PTS⁻ KLndh81 strains were inoculated into 25.0 ml of TM3 medium containing either 1% glucose or 1% fructose, and grown for 18 hr at 35° C. Sugar utilization in cells containing the galP gene driven by a constitutive promoter in TTab, compared to the native (un-induced) galP gene in KLndh81, was established by determining cell mass accumulation through optical density (A600 nm) measurements. The results in Table 12 show no significant difference in cell mass accumulation, regardless of carbohydrate source or whether the fructokinase gene was present in a strain containing a natvie galP operon, compared to constitutive galP expression.

TABLE 12

Fructose Utilization in PTS⁻ E. coli strains

| Strain | OD600 |
| --- | --- |
| KLndh81 pSYCO400/AGRO-1 Glucose | 3.0 |
| KLndh81 pSYCO400/AGRO-1 Fructose | 3.3 |
| TTab pSYCO400/AGRO-1 Glucose | 4.6 |
| TTab pSYCO400/AGRO-1 Fructose | 3.9 |

Independent cell lines, n = 2

Example 6

Increased Accumulation of Fermentation Products Through yqhE Deletion

Increased accumulation of fermentation products, using fructose as the sole carbohydrate source, was demonstrated for cells which have a partial deletion in the yqh operon. Specifically, deletion of the yqhE gene was shown to increase efficiency of fructose conversion, resulting in an increased accumulation of product.

A yqhE deletion (for reference, see GenBank®, Accession # U00096) was made by the method of Datsenko and Wanner (*Proc. Natl. Acad. Sci. USA* 97:6640-6645 (2000)). This was accomplished by placing a 553 bp yqhE coding region fragment into the FRT-CmR-FRT cassette of pKD3 (Datsenko and Wanner, supra). The cassette was amplified with the primer pair yqhEFRTF and yqhEFRTR (SEQ ID NOs:9-10) using pKD3 as the template. The primer yqhEFRTF contains 78 bp of homology to the 5' end of yqhE and 22 bp of homology to the template DNA, pKD3. The primer yqhEFRTR contains 80 bp of homology to the 3' end of yqhE and 20 bp of homology to pKD3.

The PCR products were gel purified and electroporated into competent cells of the TTab strain containing pKD46 (Datsenko and Wanner, supra). Recombinant strains were selected on LB plates with 15 mg/L of chloroamphenicol. The deletion of the yqhE gene was confirmed by PCR, using the primer pair yqh6800F and vec5 (SEQ ID NOs:11-12) and primer pair vec6 and vqh8419R (SEQ ID NOs:13-14). The Vec primers prime in the CmR gene and pair with 5' and 3' flanking sequence primers. The wild type strain will not amplify a PCR product with either of these of primer sets. The recombinant gave characteristic 673 bp and 850 bp PCR products.

The resulting recombinant strain, TTab ΔyqhE, was grown in TM3 media containing a mixed sugar feedstock of glucose and fructose or only fructose as described above. Cells were grown, harvested and prepared as described in Example 1. Cell mass accumulation was determined by optical density (A600 nm) measurements. Strains containing the native and deleted yqhE locus were tested for conversion of fructose by the methods described above. Culture supernatants were analyzed for glycerol and 1,3-Propanediol (PDO) accumulation by HPLC (see General Methods).

Data in Table 13 demonstrates conversion of fructose into product, through the use of various biocatalyst lines containing an *A. tumefaciens* scrK fructokinase gene. The parent yqhE deletion strain containing no fructokinase gene was also tested for fructose conversion. The results demonstrated that cells containing the *A. tumefaciens* scrK gene showed greatly enhanced accumulation of glycerol in media containing fructose as the sole carbohydrate, as compared to the same cell line with no fructokinase gene. Additionally, the data demonstrated an increased level of glycerol production in the yqhE deletion strain (TTab Δ yqhE) containing the fructokinase gene, compared to the line with a native yqhE locus (TTab). Glycerol accumulation was increased over 2-fold.

The results also show glycerol accumulation in media containing a mixed fructose and glucose feedstock, demonstrating enhanced utilization of fructose when the fructokinase gene is present. The level of glycerol accumulation was again shown to be higher in the deletion (TTab Δ yqhE) strain cultured in a mixed feed, as compared to the parent line (containing a native yqhE gene).

TABLE 13

Glycerol Accumulation (g/L) in yqhE knockout strains

| Source Carbohydrate | TTab pSYCO400/ AGRO-1 (Fructokinase⁺) g/L | TTab ΔyqhE pSYCO400/ AGRO-1 (Fructokinase⁺) g/L | TTab ΔyqhE pSYCO400 (Fructokinase⁻) g/L |
| --- | --- | --- | --- |
| Fructose | 1.21 | 2.49 | ND |
| Fructose + Glucose | 1.34 | 2.99 | 1.10 |

ND = not detected

In Table 13, strains TTab pSYCO400/AGRO-1 and TTab delta-yqhE pSYCO400/AGRO-1 each contain the *A. tumefaciens* scrK gene. The line TTab delta-yqhE pSYCO400 does not contain a fructokinase gene. The yqhE gene was deleted in lines TTab delta-yqhE pSYCO400/AGRO-1 and TTab delta-yqhE pSYCO400. The line TTab pSYCO400/AGRO-1 contains a native yqhE gene.

The results in Table 14 show that cells containing the *A. tumefaciens* scrK gene accumulate PDO in media containing fructose as the sole carbohydrate. Also shown is an increased conversion of fructose into product by two independently isolated strains (TTab ΔyqhE pSYCO400/AGRO-8 and TTab ΔyqhE pSYCO400/AGRO-11) containing a yqhE deletion, compared to the parent line (native yqhE).

TABLE 14

1,3-Propanediol Accumulation (g/L) in yqhE deletion strains

| Strain | 1,3-Propanediol (g/L) |
| --- | --- |
| TTab pSYCO400/AGRO-1 | 1.17 |
| TTab ΔyqhE pSYCO400/AGRO-8 | 2.71 |
| TTab ΔyqhE pSYCO400/AGRO-11 | 2.89 |

We claim:

1. A process for the microbial production of glycerol and glycerol derivatives comprising:
   (a) providing a phosphoenolpyruvate-dependent phosphotransferase system negative (PTS⁻) microorganism expressing an endogenous fructose transport protein activity wherein said microorganism is selected from the group consisting of *Escherichia, Citrobacter, Klebsiella* and *Aerobacter*;
   (b) modifying the microorganism of step (a) to increase fructokinase activity in the microorganism by expressing an *Agrobacterium* or *Streptococcus* scrK gene, which encodes a fructokinase;
   (c) culturing the microorganism of step (b) in a fructose-containing medium, whereby the microorganism utilizes fructose to produce glycerol and one or more glycerol derivatives selected from the group consisting of 3-hydroxypropionic acid (3-HPA), methylglyoxal, 1,2-propanediol, and 1,3-propanediol; and (d) optionally, recovering the glycerol or one or more glycerol derivatives selected from the group consisting of 3-hydroxypropionic acid (3-HPA), methylglyoxal, 1,2-propanediol, and 1,3-propanediol, or combinations thereof.

2. The process of claim 1, wherein the microorganism of step (a) is *Escherichia* and wherein said *Escherichia* has been modified prior to step (c) by disrupting the endogenous keto-reductase gene (yqhE gene).

3. The process of claim 1, wherein the microorganism of step (a) has been modified prior to step (c) to increase fructose transport protein activity by expressing a gene encoding a galactose-proton symporter (GalP).

4. The process of claim 1, wherein the microorganism of step (a) is *Escherichia*, and wherein said *Escherichia* has been modified prior to step (c) by:
  (i) disrupting the endogenous keto-reductase gene (yqhE gene); and
  (ii) expressing a gene encoding a galactose-proton syinporter (GalP) to increase fructose transport protein activity.

5. The process of claim 1, wherein the glycerol derivative is 1,3-propanediol.

6. The process of claim 1, wherein the fructose-containing medium comprises sugars which consist essentially of fructose.

7. The process of claim 6, wherein the sugars consist of fructose.

8. The process of claim 1, wherein the fructose-containing medium comprises a mixed sugar feed.

9. The process of claim 1, wherein the microorganism is *Escherichia coli*.

10. A process for the microbial production of glycerol and glycerol derivatives comprising:
  (a) providing a PTS– microorganism selected from the group consisting of *Escherichia, Citrobacter, Kiebsiella* and *Aerobacter;*
  (b) modifying the microorganism of step (a) to increase fructokinase activity in the microorganism by expressing an *Agrobacterium* or *Streptococcus* scrK gene, which encodes a fructokinase;
  (c) modifying the microorganism of step (b) to increase fructose transport protein activity by expressing a gene encoding a galactose-proton syinporter (GalP);
  (d) culturing the microorganism of step (c) in a fructose-containing medium, whereby the microorganism utilizes fructose to produce glycerol and one or more glycerol derivatives selected from the group consisting of 3-hydroxypropionic acid (3-HPA), methylglyoxal, 1,2-propanediol, and 1,3-propanediol; and
  (e) optionally, recovering the glycerol or one or more glycerol derivatives selected from the group consisting of 3-hydroxypropionic acid (3-HPA), methylglyoxal, 1,2-propanediol, and 1,3-propanediol, or combinations thereof.

11. The process of claim 10, wherein the fructose transport protein is encoded by the galactose-proton symporter gene of *E coli* (galP).

12. The process of claim 10 wherein the microorganism of step (a) is *Escherichia* and wherein said *Escherichia* has been modified prior to step (d) by disrupting the endogenous keto-reductase gene (yqhE gene).

13. The process of claim 10, wherein the glycerol derivative is 1,3-propanediol.

14. The process of claim 10, wherein the fructose-containing medium comprises sugars which consist essentially of fructose.

15. The process of claim 14, wherein the sugars consist of fructose.

16. The process of claim 10, wherein the fructose-containing medium comprises a mixed sugar feed.

17. The process of claim 10, wherein the microorganism is *Escherichia coli*.

* * * * *

UNITED STATES PATENT AND TRADEMARK OFFICE
CERTIFICATE OF CORRECTION

PATENT NO.        : 7,524,660 B2                                           Page 1 of 1
APPLICATION NO.   : 11/122811
DATED             : April 28, 2009
INVENTOR(S)       : Perry G. Caimi and Charles E. Nakamura It is certified that error appears in the above-identified patent and that said Letters Patent is hereby corrected as shown below:

Claim 4, column 49, lines 21-22, "syinporter" should read --symporter--.

Claim 10, column 50, line 7, "syinporter" should read --symporter--.

Signed and Sealed this

Fourteenth Day of July, 2009

JOHN DOLL
*Acting Director of the United States Patent and Trademark Office*